US005776683A

United States Patent [19]
Smith et al.

[11] Patent Number: 5,776,683
[45] Date of Patent: Jul. 7, 1998

[54] METHODS FOR IDENTIFYING GENES AMPLIFIED IN CANCER CELLS

[75] Inventors: Helene S. Smith, San Francisco; Ling-Chun Chen, Fremont, both of Calif.

[73] Assignee: California Pacific Medical Center, San Francisco, Calif.

[21] Appl. No.: 678,280

[22] Filed: Jul. 11, 1996

[51] Int. Cl.[6] .................... C12Q 1/68; C12P 19/34; C07H 21/04; C07H 21/02
[52] U.S. Cl. .................. 435/6; 435/91.2; 435/174; 435/172.3; 435/69.1; 536/23.1; 536/24.3; 536/24.33
[58] Field of Search .................. 435/6, 91.2, 174, 435/172.3, 69.1; 536/23.1, 24.3, 24.33; 514/2

[56] References Cited

U.S. PATENT DOCUMENTS

| | | |
|---|---|---|
| 4,444,887 | 4/1984 | Hoffman . |
| 4,472,500 | 9/1984 | Milstein et al. . |
| 4,491,632 | 1/1985 | Wands et al. . |
| 4,683,195 | 7/1987 | Mullis et al. . |
| 4,683,202 | 7/1987 | Mullis . |
| 4,968,603 | 11/1990 | Slamon et al. . |
| 5,124,246 | 6/1992 | Urdea et al. . |
| 5,262,311 | 11/1993 | Pardee et al. . |
| 5,324,654 | 6/1994 | Bredsen . |
| 5,399,346 | 3/1995 | Anderson et al. . |
| 5,427,932 | 6/1995 | Weier et al. . |
| 5,447,841 | 9/1995 | Gray et al. . |
| 5,472,842 | 12/1995 | Stokke et al. . |
| 5,580,726 | 12/1996 | Villeponteau et al. .............. 435/6 |

FOREIGN PATENT DOCUMENTS

| | | |
|---|---|---|
| 430402 | 6/1991 | European Pat. Off. . |
| 500290 | 8/1992 | European Pat. Off. . |
| WO 91/02062 | 2/1991 | WIPO . |
| WO 92/13091 | 8/1992 | WIPO . |
| WO 92/21771 | 12/1992 | WIPO . |
| WO 93/05149 | 3/1993 | WIPO . |
| WO 93/08701 | 5/1993 | WIPO . |
| WO 93/13204 | 7/1993 | WIPO . |
| WO 9313204 | 7/1993 | WIPO . |
| WO 93/18176 | 9/1993 | WIPO . |
| WO 93/18186 | 9/1993 | WIPO . |
| WO 94/00601 | 1/1994 | WIPO . |
| WO 94/17414 | 8/1994 | WIPO . |
| WO 94/28127 | 12/1994 | WIPO . |
| WO 95/05738 | 3/1995 | WIPO . |
| WO 95/09929 | 4/1995 | WIPO . |
| WO 95/22624 | 8/1995 | WIPO . |
| WO 95/33760 | 12/1995 | WIPO . |

OTHER PUBLICATIONS

Liang et al. Cancer Reserch 52: 6966–6968, 1992.
McClelland et al. DNA Fingerprinting : State of the Science, eds PEna et al., pp. 103–115, 1993.
Iwamura et al. Proceedings of the Am Assoc for Cancer Research vol. 36; A1351, 1995.

(List continued on next page.)

Primary Examiner—W. Gary Jones
Assistant Examiner—Dianne Rees
Attorney, Agent, or Firm—Morrison & Foerster, LLP

[57] ABSTRACT

New methods are disclosed for detecting cancer associated genes, and obtaining corresponding cDNA fragments. The methods involve supplying RNA preparations from control cells, and from a plurality of different cancer cells that share a duplicated or deleted gene in the same region of a chromosome. Amplified cDNA copies are displayed, and then selected based on differences in abundance of RNA between preparations. Optional additional screening steps involve surveying panels of cancer cells using the cDNA for RNA overabundance with or without gene duplication. By applying these methods, cDNA sequences derived from four novel genes associated with breast cancer were obtained and characterized. Each of the genes was duplicated in about 60% of the cancer cell lines tested; while other cells showed RNA overabundance without gene duplication. Genes with these properties are particularly useful in cancer diagnosis and treatment.

22 Claims, 5 Drawing Sheets

OTHER PUBLICATIONS

Bober et al. Proceedings of the Am Assoc. for Cancer Research vol. 36: A1352, 1995.

Orkin et al. Report and Recommendations to NIH, 1995.

Adane et al. "BEK and FLG, two receptors to members of the FGF family, are amplified in subsets of human breast cancers" *Oncogene* (1991) 6:659–663.

Alitalo et al., "Oncogene amplification in tumor cells" *Adv. Cancer Res.* (1986) 47:235–281.

Altschul et al., "Optimal sequence alighment using affine gap costs" *Bull. Math. Bio.* (1986) 48:603–616.

Aziz et al., "The FDA's perspective on the evaluation of tumor marker tests" *Clin. Chem.* (1993) 39:2439–2443.

Bauer et al., "Identification of differentially expressed mRNA species by an improved display technique (DDRT-–PCR)" *Nucl. Acids Res.* (1993) 21:4272–4280.

Beardsley "Crapshoot: manufacturers gamble on cancer vaccines–again" *Scientific American* (1994) Sep. 102 volume number not relevant.

Berns et al., "Sporadic amplification of the insulin–like growth factor 1 receptor gene in human breast tumors" *Cancer Res.* (1992) 52:1036–1039.

Bishop, "Molecular themes in oncogenesis" *Cell* (1991) 64:235–248.

Bast, Jr., "Perspectives on the future of cancer markers" *Clin Chem.* (1993) 39:2444–2451.

Brison, "Gene amplification and tumor progression" *Biochim. Biophys. Acta* (1993) 1155:25–41.

Cowley et al., "A vaccine for breast cancer?" *Newsweek* (Nov. 1, 1993) p. 68.

Culver et al., "Gene therapy for cancer" *Trends Genet.* (1994) 10:174–178.

Dutrillaux et al., "Characterization of chromosomal anomalies in human breast cancer" *Cancer Genet. Cytogenet.* (1990) 49:203–217.

Henikoff et al., "Amino acid substitution matrices from protein blocks" *Proc. Natl. Acad. Sci. USA* (1992) 89:10915–10919.

Kallioniemi et al., "Comparative genomic hybridization for molecular cytogenetic analysis of solid tumors" *Science* (1992) 258:818–821.

Kallioniemi et al., "Detection and mapping of amplified DNA sequences in breast cancer by comparative genomic hybridization" *Proc. Natl. Acad. Sci. USA* (1994) 91:2156–2160.

Klijn et al., "The clinical significance of epidermal growth factor receptor (EGF-R) in human breast cancer: a review on 5232 patients" *Endocrine Rev.* (1992) 13:3–17.

Liang et al., "Differential display of eukaryotic messenger RNA by means of the polymerase chain reaction" *Science* (1992) 257:967–971.

Liang et al., "Distribution and cloning of eukaryotic mRNAs by means of differential display: refinements and optimization" *Nucl. Acids Res.* (1993) 21:3269–3275.

Lippman, "The development of biological therapies for breast cancer" *Science* (1993) 259:631–632.

Lippman, "Growth factors, receptors, and breast cancer" *J. NIH Res.* (1991) 3:59–62.

MacLean et al., "The immune system, cancer antigens and immunotherapy" *Contemp. Oncol.* (Aug./Sep. 1992) pp. 1–7, vol. number not applicable.

Melillo, "Conjugate vaccine shows promise as stimulant of specific antibodies" *Internal Medicine World Report* (Jun. 1–14, 1994) p. 40, vol. number not applicable.

Mok et al., "Molecular cloning of differentially expressed genes in human epithelial ovarian cancer" *Gynecologic Oncol.* (1994) 52:247–252.

Morgan et al., "Human gene therapy" *Ann. Rev. Biochem.* (1993) 62:191–217.

Muss et al., "c–erbB–2 expression and response to adjuvant therapy in women with node–positive early breast cancer" *New Engl. J. Med.* (1994) 330:1260–1266.

Roth, "Modualtion of oncogene and tumor–suppressor gene expression: a novel strategy for cancer prevention and treatment" *Ann. Surg. Oncol.* (1994) 1:79–86.

Saint–Ruf et al., "Proto–oncogene amplification and homogeneously staining regions in human breast carcinomas" *Genes Chromosomes & Cancer* (1990) 2:18–26.

Slamon et al., "Human breast cancer: correlation of relapse and survival with amplification of the HER–2/neu oncogene" *Science* (1987) 235:178–182.

Schwab et al., "Amplification of cellular oncogenes: a predictor of clinical outcome of human cancer" *Genes Chromosomes & Cancer* (1990) 1:181–193.

Trentmann et al., "Alternatives to $^{35}$S as a label for the differential display of eukaryotic messenger RNA" *Science* (1995) 267:1186–1187.

Unsigned, "Synthetic vaccine stabilizes advanced cancer, prolongs survival" *Oncol. News Int.* (1994) 3:1.

Unsigned, "Biomira developing test for breast cancer recurrence" *Toronto Globe and Mail* (Jun. 7, 1994). 1 page total.

Watson et al., "Isolation of differentially expressed sequence tags from human breast cancer" *Cancer Res.* (1994) 54:4598–4602.

Wintersberger, "DNA amplification: New insights into its mechanism" *Chromosoma* (1994) 103:73–81.

Zafrani et al., "Cytogenetic study of breast cancer: clinicopathologic significance of homogeneously staining regions in 84 patients" *Hum. Pathol.* (1992) 23:542–547.

Ayala M. et al. (1995), "New primer strategy improves precision of differential display", BioTechniques 18:842–850.

Bertioli D.J. et al. (1995), "An analysis of differential display shows a strong bias towards high copy number mRNAs", Nucl. Acids Res. 23:4520–4523.

Chen Z. et al. (1995), "Differential expression of human tissue factor in normal mammary epithelial cells and in carcinomas", Molecular Med. 1:153–160.

Haag E. et al. (1994), "Effects of primer choice and source of Taq DNA polymerase on the binding patterns of differential display RT-PCR", BioTechniques 17:226–228.

Kocher O. et al. (1995), "Identification of a novel gene, selectivley up–regulated in human carcinomas, using the differential display technique", Clin. Cancer Res. 1:1209–1215.

Liang P. et al. (1992b), "Differential display and cloning of messenger RNAs in human breast cancer versus mammary epithelial cells", Cancer Res. 52:6966–6968.

Liang P. et al. (1994), "Differential display using one–base anchored oligo–dT primers", Nucl. Acids Res. 22:5763–5764.

Linskens M.H.K. et al. (1995), "Cataloging altered gene expression in young and senescent cells using enhanced differential display", Nucl. Acids Res. 23:3244–3251.

McKenzie D. et al. (1994), "Using the RNA arbitrarily primed polymerase chain reaction (RAP–PCR) to analyze gene expression in human breast cancer cells lines" [abstract]. J. Cell. Biochem. 18D:248.

Sunday M.E. et al. (1995), "Differential display RT-PCR for identifying novel gene expression in the lung", Am. J. Physiol. 269:L273–L284.

Yeatman T.J. et al. (1995), "Identification of a differentially-expressed message associated with colon cancer liver metastasis using an improved method of differential display", Nucl. Acids Res. 23:4007–4008.

Hadman M. et al. (1995), "Modifications to the differential display technique reduce background and increase sensitivity", Anal. Biochem. 226:383–386.

Ito T. et al. (1994), "Fluorescent differential display: arbitrarily primed RT-PCR fingerprinting on an automated DNA sequencer", FEBS Lett. 351:231–236.

Liang P. et al. (1995a), "Recent advances in differential display", Curr. Opin. Immunol. 7:274–280.

Liang P. et al (1995b), "Analysis of altered gene expression by differential display", Methods Enzymol. 254:304–321.

Snager R. et al. (1993), "Identification by differential display of alpha-6 integrin as a candidate tumor suppressor gene", FASEB J. 7:964–970.

Sompayrac L. et al. (1995), "Overcoming limitations of the mRNA differential display technique", Nucl. Acids Res. 23:4738–4739.

Thompson C.T. et al. (1993), "Cytogenetic profiling using fluorescence in situ hybridization (FISH) and comparative genomic hybridization (CGH)", J. Cell Biochem. 17G:139–143.

Welsh J. et al. (1992), "Arbitrarily primed PCR fingerprinting of RNA", Nucl. Acids Res. 20:4965–4970.

Yoshikawa T. et al. (1995), "Detection, simultaneous display and direct sequencing of multiple nuclear hormone receptor genes using bilaterally targeted RNA fingerprinting", Biochim. Biophys. Acta 1264:63–71.

EMBL Data Library Accession Number t27279 XP002019978 (1 page total).

EMBL Data Library Accession Number t27279 XP002019979 (1 page total).

Slamon et al., "Studies of the HER-2/neu proto-oncogene in human breast and ovarian cancer" *Science* (1989) 244:707–712.

Bièche et al., "Loss and gain of distinct regions of chromosome 1q in primary breast cancer" *Clinical Cancer Research* (1995) 1:123–127.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 152 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..152

( x i ) SEQUENCE DESCRIPTION: SEQ ID NO:1:

```
GA AAA CAA ATG GAA GAA ATG CAA AAG GCT TTC AAT AAA ACA ATC GTG         47
   Lys Gln Met Glu Glu Met Gln Lys Ala Phe Asn Lys Thr Ile Val
    1           5                  10                  15

AAA CTT CAG AAT ACT TCA AGA ATA GCA GAG GAG CAG GAT CAG CGG CAA         95
Lys Leu Gln Asn Thr Ser Arg Ile Ala Glu Glu Gln Asp Gln Arg Gln
            20                  25                  30

ACT GAA GCC ATC CAG TTG CTA CAG GCA CAG CTG ACC AAC ATG ACA CAG        143
Thr Glu Ala Ile Gln Leu Leu Gln Ala Gln Leu Thr Asn Met Thr Gln
                35                  40                  45

CTT GTT CAA                                                            152
Leu Val Gln
        50
```

( 2 ) INFORMATION FOR SEQ ID NO:2:

( i ) SEQUENCE CHARACTERISTICS:
        ( A ) LENGTH: 50 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Lys Gln Met Glu Glu Met Gln Lys Ala Phe Asn Lys Thr Ile Val Lys
 1               5                  10                  15

Leu Gln Asn Thr Ser Arg Ile Ala Glu Glu Gln Asp Gln Arg Gln Thr
            20                  25                  30

Glu Ala Ile Gln Leu Leu Gln Ala Gln Leu Thr Asn Met Thr Gln Leu
                35                  40                  45

Val Gln
 50
```

( 2 ) INFORMATION FOR SEQ ID NO:3:

( i ) SEQUENCE CHARACTERISTICS:
        ( A ) LENGTH: 163 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..162

( x i ) SEQUENCE DESCRIPTION: SEQ ID NO:3:

```
GAA CAG GCA AGC AGA TAT GCT ACT GTC AGT GAA AGA GTG CAT GCT CAA      48
Glu Gln Ala Ser Arg Tyr Ala Thr Val Ser Glu Arg Val His Ala Gln
                 55                  60                  65

GTG CAG CAA TTT CTA AAA GAA GGT TAT TTA AGG GAG GAG ATG GTT CTG      96
Val Gln Gln Phe Leu Lys Glu Gly Tyr Leu Arg Glu Glu Met Val Leu
             70                  75                  80

GAC AAT ATC CCA AAG CTT CTG AAC TGC CTG AGA GAC TGC AAT GTT GCC     144
Asp Asn Ile Pro Lys Leu Leu Asn Cys Leu Arg Asp Cys Asn Val Ala
         85                  90                  95

ATC CGA TGG CTG ATG CTT C                                           163
Ile Arg Trp Leu Met Leu
100
```

( 2 ) INFORMATION FOR SEQ ID NO:4:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu Gln Ala Ser Arg Tyr Ala Thr Val Ser Glu Arg Val His Ala Gln
 1               5                  10                  15

Val Gln Gln Phe Leu Lys Glu Gly Tyr Leu Arg Glu Glu Met Val Leu
             20                  25                  30

Asp Asn Ile Pro Lys Leu Leu Asn Cys Leu Arg Asp Cys Asn Val Ala
         35                  40                  45

Ile Arg Trp Leu Met Leu
50
```

( 2 ) INFORMATION FOR SEQ ID NO:5:

( i ) SEQUENCE CHARACTERISTICS:
        ( A ) LENGTH: 107 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 1..105

( x i ) SEQUENCE DESCRIPTION: SEQ ID NO:5:

```
CTC ACA ATG GGC TAC TGG CCA ACA TAC ACG CCC ATG GAA GTG CAC TTA      48
Leu Thr Met Gly Tyr Trp Pro Thr Tyr Thr Pro Met Glu Val His Leu
 55                  60                  65                  70

ACC CCA GAA ATG ATT AAA CTT CAG GAA GTA TTT AAG GCA TTT TAT CTT      96
Thr Pro Glu Met Ile Lys Leu Gln Glu Val Phe Lys Ala Phe Tyr Leu
```

```
                                    75                         80                         85
GGA  AAG  CAC  AG                                                                                           107
Gly  Lys  His
```

( 2 ) INFORMATION FOR SEQ ID NO:6:

( i ) SEQUENCE CHARACTERISTICS:
        ( A ) LENGTH: 35 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Leu  Thr  Met  Gly  Tyr  Trp  Pro  Thr  Tyr  Thr  Pro  Met  Glu  Val  His  Leu
 1                  5                        10                       15

Thr  Pro  Glu  Met  Ile  Lys  Leu  Gln  Glu  Val  Phe  Lys  Ala  Phe  Tyr  Leu
               20                       25                       30

Gly  Lys  His
          35
```

( 2 ) INFORMATION FOR SEQ ID NO:7:

( i ) SEQUENCE CHARACTERISTICS:
        ( A ) LENGTH: 114 base pairs
        ( B ) TYPE: nucleic acid
        ( C ) STRANDEDNESS: double
        ( D ) TOPOLOGY: linear ( i i ) MOLECULE TYPE: cDNA ( i x ) FEATURE:
        ( A ) NAME/KEY: CDS
        ( B ) LOCATION: 3..113

( x i ) SEQUENCE DESCRIPTION: SEQ ID NO:7:

```
TG  TTT  GTT  CAC  CCA  AAT  TGT  AAA  TAT  GAT  GCA  AAG  TGT  ACT  AAA  CCA       47
    Phe  Val  His  Pro  Asn  Cys  Lys  Tyr  Asp  Ala  Lys  Cys  Thr  Lys  Pro
                         40                       45                       50

GAT  TGT  CCC  TTC  ACT  CAT  GTG  AGT  AGA  AGA  ATT  CCA  GTA  CTG  TCT  CCA       95
Asp  Cys  Pro  Phe  Thr  His  Val  Ser  Arg  Arg  Ile  Pro  Val  Leu  Ser  Pro
                    55                       60                       65

AAA  CCA  GTT  GCA  CCA  CCA  G                                                     114
Lys  Pro  Val  Ala  Pro  Pro
                    70
```

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Phe  Val  His  Pro  Asn  Cys  Lys  Tyr  Asp  Ala  Lys  Cys  Thr  Lys  Pro  Asp
 1                  5                        10                       15

Cys  Pro  Phe  Thr  His  Val  Ser  Arg  Arg  Ile  Pro  Val  Leu  Ser  Pro  Lys
               20                       25                       30

Pro  Val  Ala  Pro  Pro
               35
```

( 2 ) INFORMATION FOR SEQ ID NO:9:

( i ) SEQUENCE CHARACTERISTICS:

(A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:9:

TTTTTTTTT TCC                                                                                  13

(2) INFORMATION FOR SEQ ID NO:10:

(i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:10:

TTTTTTTTT TAC                                                                                  13

(2) INFORMATION FOR SEQ ID NO:11:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:11:

CAATCGCCGT                                                                                     10

(2) INFORMATION FOR SEQ ID NO:12:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:12:

TCGGCGATAG                                                                                     10

(2) INFORMATION FOR SEQ ID NO:13:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:13:

CAGCACCCAC                                                                                     10

(2) INFORMATION FOR SEQ ID NO:14:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:14:

AGCCAGCGAA                                                                                     10

METHODS FOR IDENTIFYING GENES AMPLIFIED IN CANCER CELLS

REFERENCE TO GOVERNMENT GRANT

This invention was made in part during work supported by a grant from the National Cancer Institute (P01-CA44768). The Government has certain rights in the invention.

FIELD OF THE INVENTION

The present invention relates generally to the field of human genetics. More specifically, it relates to the identification and characterization of novel genes associated with overabundance of RNA in cancer; especially those genes and the products thereof which may be important in diagnosis and treatment.

BACKGROUND OF THE INVENTION

Cancer is a heterogeneous disease. It manifests itself in a wide variety of tissue sites, with different degrees of de-differentiation, invasiveness, and aggressiveness. Some forms of cancer are responsive to traditional modes of therapy, but many are not. For most common cancers, there is a pressing need to improve the arsenal of therapies available to provide more precise and more effective treatment in a less invasive way.

As an example, breast cancer has an unsatisfactory morbidity and mortality, despite presently available forms of medical intervention. Traditional clinical initiatives are focused on early diagnosis, followed by surgery and chemotherapy. Such interventions are of limited success, particularly in patients where the tumor has undergone metastasis.

The heterogeneous nature of cancer arises because different cancer cells achieve their growth and pathological properties by different phenotypic alterations. Alteration of gene expression is intimately related to the uncontrolled growth and de-differentiation that are hallmarks of cancer. Certain similar phenotypic alterations in turn may have a different genetic base in different tumors. Yet, the number of genes central to the malignant process must be a finite one. Accordingly, new pharmaceuticals that are tailored to specific genetic alterations in an individual tumor may be more effective.

There are two types of altered gene expression that take place, together or independently, in different cancer cells (Bishop). The first type is the decreased expression of recessive genes, known as tumor suppresser genes, that apparently act to prevent malignant growth. The second type is the increased expression of dominant genes, such as oncogenes, that act to promote malignant growth, or to provide some other phenotype critical for malignancy. Thus, alteration in the expression of either type of gene is a potential diagnostic indicator. Furthermore, a treatment strategy might seek to reinstate the expression of suppresser genes, or reduce the expression of dominant genes. The present invention is directed to identifying genes of either type, particularly those of the second type.

The most frequently studied mechanism for gene overexpression in cancer cells is sometimes referred to as amplification. This is a process whereby the gene is duplicated within the chromosomes of the ancestral cell into multiple copies. The process involves unscheduled replications of the region of the chromosome comprising the gene, followed by recombination of the replicated segments back into the chromosome (Alitalo et al.). As a result, 50 or more copies of the gene may be produced. The duplicated region is sometimes referred to as an "amplicon". The level of expression of the gene (that is, the amount of messenger RNA produced) escalates in the transformed cell in the same proportion as the number of copies of the gene that are made (Alitalo et al.).

Several human oncogenes have been described, some of which are duplicated, for example, in a significant proportion of breast tumors. A prototype is the erbB2 gene (also known as HER-2/neu), which encodes a 185 kDa membrane growth factor receptor homologous to the epidermal growth factor receptor. erbB2 is duplicated in 61 of 283 tumors (22%) tested in a recent survey (Adnane et al.). Other oncogenes duplicated in breast cancer are the bek gene, duplicated in 34 out of 286 (12%); the flg gene, duplicated in 37 out of 297 (12%), the myc gene, duplicated in 43 out of 275 (16%) (Adnane et al.).

Work with other oncogenes, particularly those described for neuroblastoma, suggested that gene duplication of the proto-oncogene was an event involved in the more malignant forms of cancer, and could act as a predictor of clinical outcome (reviewed by Schwab et al. and Alitalo et al.). In breast cancer, duplication of the erbB2 gene has been reported as correlating both with reoccurrence of the disease and decreased survival times (Slamon et al.). There is some evidence that erbB2 helps identify tumors that are responsive to adjuvant chemotherapy with cyclophosphamide, doxorubicin, and fluorouracil (Muss et al.).

It is clear that only a proportion of the genes that can undergo gene duplication in cancer have been identified. First, chromosome abnormalities, such as double minute (DM) chromosomes and homogeneously stained regions (HSRs), are abundant in cancer cells. HSRs are chromosomal regions that appear in karyotype analysis with intermediate density Giemsa staining throughout their length, rather than with the normal pattern of alternating dark and light bands. They correspond to multiple gene repeats. HSRs are particularly abundant in breast cancers, showing up in 60–65% of tumors surveyed (Dutrillaux et al., Zafrani et al.). When such regions are checked by in situ hybridization with probes for any of 16 known human oncogenes, including erbB2 and myc, only a proportion of tumors show any hybridization to HSR regions. Furthermore, only a proportion of the HSRs within each karyotype are implicated.

Second, comparative genomic hybridization (CGH) has revealed the presence of copy number increases in tumors, even in chromosomal regions outside of HSRs. CGH is a new method in which whole chromosome spreads are stained simultaneously with DNA fragments from normal cells and from cancer cells, using two different fluorochromes. The images are computer-processed for the fluorescence ratio, revealing chromosomal regions that have undergone amplification or deletion in the cancer cells (Kallioniemi et al. 1992). This method was recently applied to 15 breast cancer cell lines (Kallioniemi et al. 1994). DNA sequence copy number increases were detected in all 23 chromosome pairs.

Cloning the genes that undergo duplication in cancer is a formidable challenge. In one approach, human oncogenes have been identified by hybridizing with probes for other known growth-promoting genes, particularly known oncogenes in other species. For example, the erbB2 gene was identified using a probe from a chemically induced rat neuroglioblastoma (Slamon et al.). Genes with novel sequences and functions will evade this type of search. In another approach, genes may be cloned from an area identified as containing a duplicated region by CGH method. Since CGH is able to indicate only the approximate chromosomal region of duplicated genes, an extensive amount of experimentation is required to walk through the entire region and identify the particular gene involved.

Genes may also be overexpressed in cancer without being duplicated. Methods that rely on identification from genetic abnormalities necessarily bypass such genes. Increased expression can come about through a higher level of transcription of the gene; for example, by up-regulation of the promoter or substitution with an alternative promoter. It can also occur if the transcription product is able to persist longer in the cell; for example, by increasing the resistance to cytoplasmic RNase or by reducing the level of such cytoplasmic enzymes. Two examples are the epidermal growth factor receptor, overexpressed in 45% of breast cancer tumors (Klijn et al.), and the IGF-1 receptor, overexpressed in 50–93% of breast cancer tumors (Berns et al.). In almost all cases, the overexpression of each of these receptors is by a mechanism other than gene duplication.

One way of examining overexpression at the messenger RNA level is by subtractive hybridization. It involves producing positive and negative cDNA strands from two RNA preparations, and looking for cDNA which is not completely hybridized by the opposing preparation. This is a laborious procedure which has distinct limitations in cancer research. In particular, since each subtraction involves cDNA from only two cell populations at a time, it is sensitive to individual phenotypic differences due not just to the presence of cancer, but also through natural metabolic variations.

Another way of examining overexpression at the messenger RNA level is by differential display (Liang et al. 1992a). In this technique, cDNA is prepared from only a subpopulation of each RNA preparation, and expanded via the polymerase chain reaction using primers of particular specificity. Similar subpopulations are compared across several RNA preparations by gel autoradiography for expression differences. In order to survey the RNA preparations entirely, the assay is repeated with a comprehensive set of PCR primers. The screening strategy more effectively includes multiple positive and negative control samples (Sunday et al.). The method has recently been applied to breast cancer cell lines, and highlights a number of expression differences (Liang et al. 1992b; Chen et al., McKenzie et al., Watson et al. 1994 & 1996, Kocher et al.). By excising the corresponding region of the separating gel, it is possible to recover and sequence the cDNA.

Despite the advancement provided by differential display, problems remain in terms of applying it in the search for new cancer genes. First, because this is a test for RNA levels, any phenotypic difference between cell lines constitute part of the recovered set, leading to a large proportion of "false positive" identifications. We have found that cDNA for mitochondrial genes constitute a large proportion of the differentially expressed bands, and it consumes substantial resources to recover the sample and obtain a partial sequence in order to eliminate them. Second, false positive identifications are made for reasons attributed to multiple cDNA species and competition for the PCR primers by RNA species of different abundance (Debouck). Third, differential display highlights high copy number mRNAs and shorter mRNAs (Bertioli et al., Yeatman et al.), and may therefore miss critical cancer-associated transcripts when used as a survey technique. Fourth, a number of adjustments are made to gene expression levels when a cell undergoes malignant transformation or cultured in vitro. Most of these adjustments are secondary, and not part of the transformation process. Thus, even when a novel sequence is obtained from the differential display, it is far from certain that the corresponding gene is at the root of the disease process.

An early step in developing gene-specific therapeutic approaches is the identification of genes that are more central to malignant transformation or the persistence of the malignant phenotype.

SUMMARY OF THE INVENTION

It is an objective of this invention to provide a method for identifying and characterizing genes and gene products which are duplicated or associated with overabundant RNA in cancer cells. The method can be used for any type of cancer, providing a plurality of cell populations or cell lines of the type of cancer are available, in conjunction with a suitable control cell population. The method is highly effective in identifying genes and gene products that are intimately related to malignant transformation or maintenance of the malignant properties of the cancer cells.

An important derivative of applying the method is the selection and retrieval of cDNA and cDNA fragments corresponding to the cancer-associated gene. These fragments can be used inter alia to determine the nucleotide sequence of the gene and mRNA, the amino acid sequence of any encoded protein, or to retrieve from a cDNA or genomic library additional polynucleotides related to the gene or its transcripts. Since the genes are typically involved in the malignant process of the cell, the polynucleotides, polypeptides, and antibodies derived by using this method can in turn be used to design or screen important diagnostic reagents and therapeutic compounds.

Accordingly, embodiments of this invention are methods for obtaining cDNA corresponding to a gene associated with cancer, comprising the steps of: a) supplying an RNA preparation from uncultured control cells; b) supplying RNA preparations from at least two different cancer cells; c) displaying cDNA corresponding to the RNA preparations of step a) and step b) such that different cDNA corresponding to different RNA in each preparation are displayed separately; d) selecting cDNA corresponding to RNA that is present in greater abundance in the cancer cells of step b) relative to the control cells of step a); e) supplying a digested DNA preparation from control cells; f) supplying digested DNA preparations from at least two different cancer cells; g) hybridizing the cDNA of step d) with the digested DNA preparations of step e) and step f); and h) further selecting cDNA from the cDNA of step d) corresponding to genes that are duplicated in the cancer cells of step f) relative to the control cells of step e).

When used in referring to the gene screening methods of this invention (such as those outlined in the last paragraph), "displaying cDNA" is any technique in which DNA copies of RNA (not restricted to mRNA) is rendered detectable in a quantitative or relatively quantitative fashion, in that DNA copies present in a relatively greater amount in a first sample compared with a second sample generates a relatively stronger or weaker signal compared with that of the second sample due to the difference in copy number. Separate display of different cDNA in a preparation (particularly but not limited to cDNA of different size) allows comparison of levels of a particular cDNA between different samples. A preferred method of display is the differential display technique, and enhancements thereupon described in this disclosure and elsewhere. "Digested" DNA encompasses DNA particularly chromosomal DNA) that has been fragmented by any suitable chemical or enzymatic means into fragments conveniently separable by standard techniques, particularly gel electrophoresis. Digestion with a restriction endonuclease specific for a particular nucleotide sequence is preferred. "Hybridizing" in this context refers to contacting a first polynucleotide with a second polynucleotide under conditions that permit the formation of a multi-stranded polynucleotide duplex whenever one strand of the first polynucleotide has a sequence of sufficient complementarity to a sequence on the second polynucleotide. The duplex may be a long-lived one, such as when one DNA molecule is used as a labeled probe to detect another DNA molecule, that may optionally be bound to a nitrocellulose filter or present in a separating gel. The duplex may also be a shorter-lived one, such as when one DNA molecule is used to prime an amplification reaction of the other DNA molecule, and the amplified product is subsequently detected. The practitioner may alter the conditions of the reaction to alter the degree of complementarity required, as long as sequence specificity remains a determining factor in the reaction.

Unless explicitly indicated or otherwise required by the techniques used, the steps of a method of this invention may be performed in any order, or combined where desired and appropriate. In one example, in the method comprising steps a) through h) that is described above, it is entirely appropriate to conduct steps a) to c) of the method either before or after steps e) to g) of the method, as long as the cDNA ultimately selected fulfills the criteria of both steps d) and step h). In another example, screening against different digested DNA preparations, even if outlined separately, may optionally be done at the same time. All permutations of this kind are within the scope of the invention.

One or more enhancements may optionally be included in the methods of this invention, including the following:

1. Cancer cells are preferably used for step b) that share a duplicated gene in the same region of a chromosome. If desired, the practitioner may test cancer cells beforehand to detect the duplication or deletion of chromosome regions; or cancer cell lines may be used that have already been characterized in this respect.

2. A higher plurality of cancer cells are preferably used to provide DNA for step b), step f), or preferably both step b) and step f). The use of three cancer cells is preferred over two; the use of four cancer cells is more preferred, about five cancer cells is still more preferred, about eight cancer cells is even more preferred. The cDNA of each cancer cell population is displayed or hybridized separately, in accordance with the method.

3. A higher plurality of control cells are preferably used to provide DNA for step a), step e), or preferably both step a) and step e). The use of two control cell populations is preferred; the use of three or more is even more preferred. Both proliferating and non-proliferating populations are preferably used, if available.

4. The control cells are preferably supplied fresh from a tissue source, and are not cultured or transformed into a cell line. This is increasingly important when the control cell populations used in step a) is only one or two in number. Freshly obtained cancer cells may also be used as an alternative to cancer cell lines, although this is less critical.

5. An additional screening step is preferably conducted in which the cDNA corresponding to the putative cancer-associated gene is additionally hybridized with a digested mitochondrial DNA preparation, to eliminate mitochondrial genes. This screening step may be conducted before, between, subsequent to, or simultaneously with the other screening steps of the method.

6. An additional screening step is preferably conducted in which RNA is supplied from a plurality of cancer cells, and one or preferably more control cell populations; the RNA is contacted with cDNA corresponding to the putative cancer-associated gene under conditions that permit formation of a stable duplex, and cDNA is selected corresponding to RNA that is present in greater abundance in a proportion of the cancer cells relative to the control cells. Preferably, the plurality of cancer cells is a panel of at least five, preferably at least ten cells. Preferably at least three, more preferably at least five of the cancer cells show greater abundance of RNA. Preferably at least one and preferably more of the cancer cells shows a greater abundance of RNA compared with control cells, but does not show duplication of the corresponding gene in step h) of the method.

Other embodiments of the invention are methods for obtaining cDNA corresponding to a gene that is deleted or underexpressed in cancer, comprising the steps of: a) supplying an RNA preparation from control cells; b) supplying RNA preparations from at least two different cancer cells that share a deleted gene in the same region of a chromosome; c) displaying cDNA corresponding to the RNA preparations of step a) and step b) such that different cDNA corresponding to different RNA in each preparation are displayed separately; and d) selecting cDNA corresponding to RNA that is present in lower abundance in the cancer cells of step b) relative to the control cells of step a). Such methods optionally comprise the steps of: e) supplying a digested DNA preparation from control cells; f) supplying digested DNA preparations from at least two different cancer cells; g) hybridizing the cDNA of step d) with the digested DNA preparations of step e) and step f); and h) further selecting cDNA from the cDNA of step d) corresponding to a gene that is deleted in the cancer cells of step f) relative to the control cells of step e). Such methods for identifying deleted or underexpressed genes may also comprise enhancements such as those described above.

Additional embodiments of this invention are methods for characterizing cancer genes, comprising obtaining cDNA corresponding to a cancer-associated gene according to a method of this invention, particularly those highlighted above, and then sequencing the cDNA. Alternatively or in addition, the cDNA may be used to rescue additional polynucleotides corresponding to a cancer-associated gene from an mRNA preparation, or a cDNA or genomic DNA library.

Additional embodiments of this invention are methods for screening candidate drugs for cancer treatment, comprising obtaining cDNA corresponding to a gene that is duplicated, overexpressed, deleted, or underexpressed in cancer, and comparing the effect of the candidate druge on a cell genetically altered with the cDNA or fragment thereof with the effect on a cell not genetically altered.

Various embodiments of this invention may be employed in pursuit of any form of cancer for which suitable tissue sources are available. Cancers of particular interest include lung cancer, glioblastoma, pancreatic cancer, colon cancer, prostate cancer, hepatoma, myeloma, and especially breast cancer.

BRIEF DESCRIPTION OF FIGURES

FIG. 6 is a listing of partial nucleotide and amino acid sequences for the exemplary breast cancer genes CH1-9a11-2, CH8-2a13-1, CH13-2a12-1, and CH14-2a16-1.

DETAILED DESCRIPTION OF THE INVENTION

Figure 1:
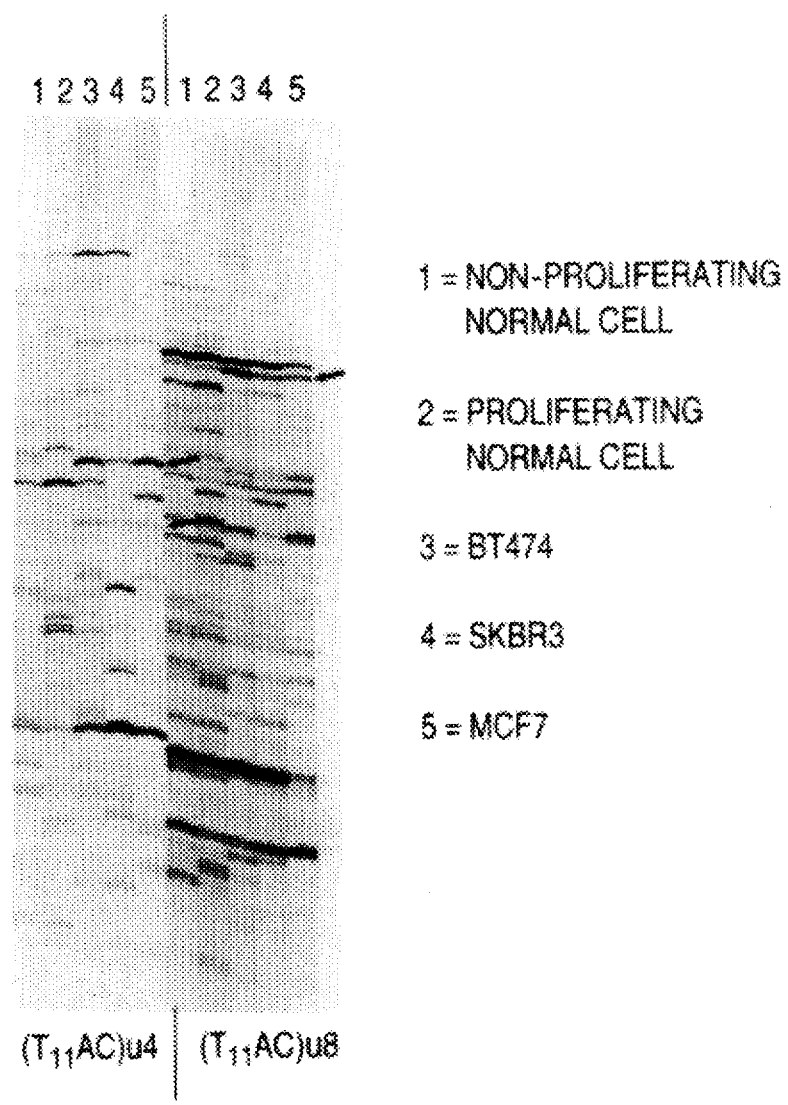
FIG. 1 is a half-tone reproduction of an autoradiogram of a differential display experiment, in which radiolabeled cDNA corresponding to a subset of total messenger RNA in different cells are compared. This is used to select cDNA corresponding to particular RNA that are overabundant in breast cancer.

This invention allows for easy and rapid identification of novel genes that are expressed at an elevated level cancer. Since abnormal gene regulation is central to the malignant process, the identification method may be brought to bear on any type of cancer. Once identified, cancer-associated genes may be characterized for a number of different purposes. For example, they may be sequenced, and the sequence data may be used to develop screening methods, design or test new pharmaceutical compositions, and determine the underlying pathology mediated by the gene.

The screening method is superior to any previously available approach in several respects. Particularly significant is that screening is rapidly focused towards genes that are central to the malignant process, and away from those that have variable levels of expression as part of normal metabolic processes. Furthermore, because the end-product is a cDNA corresponding to the gene, the process leads rapidly to detailed characterization of the gene, and any effector molecule it may encode.

Near the heart of this approach are several concepts. One is that genes encoding products implicated positively in the malignant process achieve elevated gene expression as a part of malignant transformation. In this context, "gene expression" refers to expression at the RNA transcription level. Most typically, the RNA is in turn be translated into a protein with a particular enzymatic, binding, or regulatory activity which increases after malignant transformation. Alternatively, the RNA may encode or participate as a ribozyme, antisense polynucleotide, or other functional nucleic acid molecule during malignancy. In a third example, RNA expression may be incidental but symptomatic of an important event in transformation.

Another concept is that overexpression, if central to malignant transformation, may be achieved in different tumors by different mechanisms, and that at least one such possible mechanism is gene duplication. Accordingly, a substantial proportion of transformed cells will have an amplicon, or duplicated region of a chromosome, that includes within its compass the overexpressed gene. Other transformed cells may achieve RNA overabundance without gene duplication, such as by increasing the rate of transcription of the gene (e.g., by upregulation of the promoter region), by enhancing transcript promotion or transport, or by increasing mRNA survival.

Thus, the method minimally entails screening at the RNA level, several cancer cell lines or tumors, and several normal cell lines or tissue samples at the same time. RNA are selected that show a consistent elevation amongst the cancer cells as compared with normal cells.

Additional strategies may optionally be employed in combination with the RNA screening to improve the success rate of the method. One such strategy is to use several cancer cell lines that are all known to have duplicated genes in the same region of a particular chromosome. Thus, the RNA that emerge from the screen are more likely to represent a deliberate overexpression event, and the overexpressed gene is likely to be within the duplicated region. A second supplemental strategy is to use freshly prepared tissue samples rather than cell lines as controls for base-line expression. This avoids selection of genes that may alter their expression level just as a result of tissue culturing. A third supplemental strategy is to conduct an additional level of screening, following identification of shared, overexpressed RNA. The selected RNA are used to screen DNA from suitable cancer cells and normal cells, to ensure that at least a proportion of the cells achieved the overexpression by way of gene duplication.

These strategies are surprisingly effective in identifying genes that seem to be central to the neoplastic status of the cell, and not just overexpressed as a result of normal phenotypic variation or manipulation. We were rapidly able to identify and begin characterization of four genes that are duplicated and/or overexpressed in breast cancer. The exemplary breast cancer genes are herein designated CH1-9a11-2, CH8-2a13-1, CH13-2a12-1, or CH14-2a16-1. The cDNA of these genes, and their sequences as disclosed below, provide the basis of a series of reagents that can be used in diagnosis and therapy.

Using a panel of about 15 cancer cell lines, each of the four genes was found to be duplicated in 40–60% of the cells tested. We were surprised to find that each of the four genes was duplicated in at least one cell line where studies using comparative genomic hybridization had not revealed any amplification of the corresponding chromosomal region. In addition, about 17–37% of the lines showed RNA overabundance without gene duplication, indicating that the malignant cells had used some mechanism other than gene duplication to promote the abundance of RNA corresponding to these genes. Since the genes that achieve RNA overabundance by several mechanisms, they are more likely to be directly involved in the pathogenic process, and therefore suitable targets for pharmacological manipulation.

Features of the four novel genes, the respective mRNA, and the cDNA used to find them are provided in Table 1.

TABLE 1

Characteristics of 4 Novel Breast Cancer Genes

| Chromosome | Designation | mRNA Observed | Exemplary cDNA Fragments Cloned |
|---|---|---|---|
| 1 | CH1-9a11-2 | 5.5kb, 4.5kb | 1.1kb, 2.5kb |
| 8 | CH8-2a13-1 | 4.2kb | 0.6kb (two), 3.0kb, 4.0kb |
| 13 | CH13-2a12-1 | 3.5kb, 3.2kb | 1.6kb, 3.5kb |
| 14 | CH14-2a16-1 | 3.8kb, 3kb | 0.8kb, 1.3kb, 1.6kb, 2.5kb |

Definitions

The term "polynucleotide" refers to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term polynucleotide, as used herein, refers interchangeably to double- and single-stranded molecules. Unless otherwise specified or required, any embodiment of the invention described herein that is a polynucleotide encompasses both the double-stranded form, and each of two complementary single-stranded forms known or predicted to make up the double-stranded form.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

"Hybridization" refers to a reaction in which one or more polynucleotides react to form a complex that is stabilized via hydrogen bonding between the bases of the nucleotide residues. The hydrogen bonding is sequence-specific, and typically occurs by Watson-Crick base pairing. A hybridization reaction may constitute a step in a more extensive process, such as the initiation of a PCR, or the enzymatic cleavage of a polynucleotide by a ribozyme.

Hybridization reactions can be performed under conditions of different "stringency". Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. Conditions that increase the stringency of a hybridization reaction are widely known and published in the art: see, for example, "Molecular Cloning: A Laboratory Manual", Second Edition (Sambrook, Fritsch & Maniatis, 1989).

When hybridization occurs in an antiparallel configuration between two single-stranded polynucleotides, those polynucleotides are described as "complementary". A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonding with each other, according to generally accepted base-pairing rules.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotides, the sequence for the DNA reflects the order of nitrogenous bases in the polydeoxyribonucleotides, and the two sequences satisfy the other requirements of this definition. Where one or both of the polynucleotides being compared is double-stranded, the sequences are identical if one strand of the first polynucleotide is identical with one strand of the second polynucleotide.

A linear sequence of nucleotides is "essentially identical" to another linear sequence, if both sequences are capable of hybridizing to form a duplex with the same complementary polynucleotide. Sequences that hybridize under conditions of greater stringency are more preferred. It is understood that hybridization reactions can accommodate insertions, deletions, and substitutions in the nucleotide sequence. In determining whether polynucleotide sequences are essentially identical, a sequence that preserves the functionality of the polynucleotide with which it is being compared is particularly preferred. Functionality may be established by different criteria, such as ability to hybridize with a target polynucleotide, and whether the polynucleotide encodes an identical or essentially identical polypeptides.

A "reagent" polynucleotide, polypeptide, or antibody, is a substance provided for a reaction, the substance having some known and desirable parameters for the reaction. A reaction mixture may also contain a "target", such as a polynucleotide, antibody, or polypeptide that the reagent is capable of reacting with. For example, in some types of diagnostic tests, the amount of the target in a sample is determined by adding a reagent, allowing the reagent and target to react, and measuring the amount of reaction product. In the context of clinical management, a "target" may also be a cell, collection of cells, tissue, or organ that is the object of an administered substance, such as a pharmaceutical compound.

"cDNA" or "complementary DNA" is a single- or double-stranded DNA polynucleotide in which one strand is complementary to an RNA, typically but not limited to a messenger RNA. "Full-length cDNA" is cDNA comprised of a strand which is complementary to an entire RNA molecule. A "cDNA fragment" as used herein generally represents a sub-region of the full-length form, but the entire full-length cDNA may also be included. Unless explicitly specified, the term cDNA encompasses both the full-length form and the fragment form.

Different polynucleotides are said to "correspond" to each other if one is ultimately derived from another. For example, messenger RNA corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. Polynucleotides may be said to correspond even when one of the pair is derived from only a portion of the other.

A "probe" when used in the context of polynucleotide manipulation refers to a polynucleotide which is provided as a reagent to detect a target potentially present in a sample of interest by hybridizing with the target. Usually, a probe will comprise a label or a means by which a label can be attached, either before or subsequent to the hybridization reaction. Suitable labels include, but are not limited to radioisotopes, fluorochromes, chemiluminescent compounds, dyes, and enzymes.

A "primer" is a short polynucleotide, generally with a free 3' -OH group, that binds to a target potentially present in a sample of interest by hybridizing with the target, and thereafter promoting polymerization of a polynucleotide complementary to the target. A "polymerase chain reaction" ("PCR") is a reaction in which replicate copies are made of a target polynucleotide using one or more primers, and a catalyst of polymerization, such as a reverse transcriptase or a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "replication."

An "operon" is a genetic region comprising a gene encoding a protein and functionally related 5' and 3' flanking regions. Elements within an operon include but are not limited to promoter regions, enhancer regions, repressor binding regions, transcription initiation sites, ribosome binding sites, translation initiation sites, protein encoding regions, introns and exons, and termination sites for transcription and translation. A "promoter" is a DNA region capable under certain conditions of binding RNA polymerase and initiating transcription of a coding region located downstream (in the 3' direction) from the promoter.

"Operatively linked" refers to a juxtaposition of genetic elements, wherein the elements are in a relationship permitting them to operate together. For instance, a promoter is operatively linked to a coding region if the promoter helps initiate transcription of the coding sequence. There may be intervening residues between the promoter and coding region so long as this functional relationship is maintained.

"Gene duplication" is a term used herein to describe the process whereby an increased number of copies of a particular gene or a fragment thereof is present in a particular cell or cell line. "Gene amplification" generally is synonymous with gene duplication.

"Expression" is defined alternately in the scientific literature either as the transcription of a gene into an RNA polynucleotide, or as the transcription and subsequent translation into a polypeptide. Unless otherwise stated or required, "expression" or "gene expression" when used herein refers primarily to the production of the RNA. Thus, "overexpression" reflects the presence of more RNA (as a proportion of total RNA) from a particular gene in a cell being described, such as a cancerous cell, in relation to that of the cell it is being compared with, such as a non-cancerous cell. The protein product of the gene may or may not be produced in normal or abnormal amounts. "Protein overexpression" similarly reflects the presence of relatively more protein present in or produced by, for example, a cancerous cell.

"Abundance" of RNA refers to the amount of a particular RNA present in a particular cell type. Thus, "RNA overabundance" or "overabundance of RNA" describes RNA that is present in greater proportion of total RNA in the cell type being described, compared with the same RNA as a proportion of the total RNA in a control cell. A number of mechanisms may contribute to RNA overabundance in a particular cell type: for example, gene duplication, increased level of transcription of the gene, increased persistence of the RNA within the cell after it is produced, or any combination of these. Similarly, "lower abundance" or "underabundance" describes RNA that is present in lower proportion in the cell being described compared with a control cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component.

In the context of polypeptides, a "linear sequence" or a "sequence" is an order of amino acids in a polypeptide in an N-terminal to C-terminal direction in which residues that neighbor each other in the sequence are contiguous in the primary structure of the polypeptide. A "partial sequence" is a linear sequence of part of a polypeptide which is known to comprise additional residues in one or both directions.

A linear sequence of amino acids is "essentially identical" to another sequence if the two sequences have a substantial degree of sequence identity. It is understood that functional proteins can accommodate insertions, deletions, and substitutions in the amino acid sequence. Thus, linear sequences of amino acids can be essentially identical even if some of the residues do not precisely correspond or align. Sequences that correspond or align more closely to the invention disclosed herein are more preferred. Methods for determining homologous regions and scoring the degree of homology are well known in the art; see for example Altschul et al. and Henikoff et al. Well-tolerated sequence differences are referred to as "conservative substitutions", and are preferred over other substitutions. In determining whether polypeptide sequences are essentially identical, a sequence that preserves the functionality of the polypeptide with which it is being compared is particularly preferred.

An "antibody" (interchangeably used in plural form) is an immunoglobulin molecule capable of specific binding to a target, such as a polypeptide, through at least one antigen recognition site, located in the variable region of the immunoglobulin molecule. As used herein, the term encompasses not only intact antibodies, but also fragments thereof, mutants thereof, fusion proteins, humanized antibodies, and any other modified configuration of the immunoglobulin molecule that comprises an antigen recognition site of the required specificity.

The term "antigen" refers to the target molecule that is specifically bound by an antibody through its antigen recognition site. The antigen may, but need not be chemically related to the immunogen that stimulated production of the antibody. The antigen may be polyvalent, or it may be a monovalent hapten. Examples of kinds of antigens that can be recognized by antibodies include polypeptides, polynucleotides, other antibody molecules, oligosaccharides, complex lipids, drugs, and chemicals. An "immunogen" is an antigen capable of stimulating production of an antibody when injected into a suitable host, usually a mammal. Compounds may be rendered immunogenic by many techniques known in the art, including crosslinking or conjugating with a carrier to increase valency, mixing with a mitogen to increase the immune response, and combining with an adjuvant to enhance presentation.

An "active vaccine" is a pharmaceutical preparation for human or animal use, which is used with the intention of eliciting a specific immune response. The immune response may be either humoral or cellular, systemic or secretory. The immune response may be desired for experimental purposes, for the treatment of a particular condition, for the elimination of a particular substance, or for prophylaxis against a particular condition or substance.

An "isolated" polynucleotide, polypeptide, protein, antibody, or other substance refers to a preparation of the substance devoid of at least some of the other components that may also be present where the substance or a similar substance naturally occurs or is initially obtained from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred. A substance can also be provided in an isolated state by a process of artificial assembly, such as by chemical synthesis or recombinant expression.

A polynucleotide used in a reaction, such as a probe used in a hybridization reaction, a primer used in a PCR, or a polynucleotide present in a pharmaceutical preparation, is referred to as "specific" or "selective" if it hybridizes or reacts with the intended target more frequently, more rapidly, or with greater duration than it does with alternative substances. Similarly, an antibody is referred to as "specific" or "selective" if it binds via at least one antigen recognition site to the intended target more frequently, more rapidly, or with greater duration than it does to alternative substances. A polynucleotide or antibody is said to "selectively inhibit" or "selectively interfere with" a reaction if it inhibits or interferes with the reaction between particular substrates to a greater degree or for a greater duration than it does with the reaction between alternative substrates. An antibody is capable of "specifically delivering" a substance if it conveys or retains that substance near a particular cell type more frequently than to other cell types.

The "effector component" of a pharmaceutical preparation is a component which modifies target cells by altering their function in a desirable way when administered to a subject bearing the cells. Some advanced pharmaceutical preparations also have a "targeting component", such as an antibody, which helps deliver the effector component more efficaciously to the target site. Depending on the desired action, the effector component may have any one of a number of modes of action. For example, it may restore or enhance a normal function of a cell, it may eliminate or suppress an abnormal function of a cell, or it may alter a cell's phenotype. Alternatively, it may kill or render dormant a cell with pathological features, such as a cancer cell. Examples of effector components are provided in a later section.

A "pharmaceutical candidate" or "drug candidate" is a compound believed to have therapeutic potential, that is to be tested for efficacy. The "screening" of a pharmaceutical candidate refers to conducting an assay that is capable of evaluating the efficacy and/or specificity of the candidate. In this context, "efficacy" refers to the ability of the candidate to effect the cell or organism it is administered to in a beneficial way: for example, the limitation of the pathology of cancerous cells.

A "cell line" or "cell culture" denotes higher eukaryotic cells grown or maintained in vitro. It is understood that the descendants of a cell may not be completely identical (either morphologically, genotypically, or phenotypically) to the parent cell. Cells described as "uncultured" are obtained directly from a living organism, and have been maintained for a limited amount of time away from the organism: not long enough or under conditions for the cells to undergo substantial replication.

"Genetic alteration" refers to a process wherein a genetic element is introduced into a cell other than by natural cell division. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, contacting with a polynucleotide-liposome complex, or by transduction or infection with a DNA or RNA virus or viral vector. The alteration is preferably but not necessarily inheritable by progeny of the altered cell.

A "host cell" is a cell which has been genetically altered, or is capable of being genetically altered, by administration of an exogenous polynucleotide.

The terms "cancerous cell" or "cancer cell", used either in the singular or plural form, refer to cells that have undergone a malignant transformation that makes them pathological to the host organism. Malignant transformation is a single- or multi-step process, which involves in part an alteration in the genetic makeup of the cell and/or the expression profile. Malignant transformation may occur either spontaneously, or via an event or combination of events such as drug or chemical treatment, radiation, fusion with other cells, viral infection, or activation or inactivation of particular genes. Malignant transformation may occur in vivo or in vitro, and can if necessary be experimentally induced.

A frequent feature of cancer cells is the tendency to grow in a manner that is uncontrollable by the host, but the pathology associated with a particular cancer cell may take another form, as outlined below. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells.

The "pathology" caused by a cancer cell within a host is anything that compromises the well-being or normal physiology of the host. This may involve (but is not limited to) abnormal or uncontrollable growth of the cell, metastasis, release of cytokines or other secretory products at an inappropriate level, manifestation of a function inappropriate for its physiological milieu, interference with the normal function of neighboring cells, aggravation or suppression of an inflammatory or immunological response, or the harboring of undesirable chemical agents or invasive organisms.

"Treatment" of an individual or a cell is any type of intervention in an attempt to alter the natural course of the individual or cell. For example, treatment of an individual may be undertaken to decrease or limit the pathology caused by a cancer cell harbored in the individual. Treatment includes (but is not limited to) administration of a composition, such as a pharmaceutical composition, and may be performed either prophylactically, or subsequent to the initiation of a pathologic event or contact with an etiologic agent. Effective amounts used in treatment are those which are sufficient to produce the desired effect, and may be given in single or divided doses.

A "control cell" is an alternative source of cells or an alternative cell line used in an experiment for comparison purposes. Where the purpose of the experiment is to establish a base line for gene copy number or expression level, it is generally preferable to use a control cell that is not a cancer cell.

The term "cancer gene" as used herein refers to any gene which is yielding transcription or translation products at a substantially altered level or in a substantially altered form in cancerous cells compared with non-cancerous cells, and which may play a role in supporting the malignancy of the cell. It may be a normally quiescent gene that becomes activated (such as a dominant proto-oncogene), it may be a gene that becomes expressed at an abnormally high level (such as a growth factor receptor), it may be a gene that becomes mutated to produce a variant phenotype, or it may be a gene that becomes expressed at an abnormally low level (such as a tumor suppresser gene). The present invention is primarily directed towards the discovery of genes in the first two categories.

It is understood that a "clinical sample" encompasses a variety of sample types obtained from a subject and useful in an in vitro procedure, such as a diagnostic test. The definition encompasses solid tissue samples obtained as a surgical removal, a pathology specimen, or a biopsy specimen, tissue cultures or cells derived therefrom and the progeny thereof, and sections or smears prepared from any of these sources. The clinical sample may but does not necessarily comprise cancer cells. The definition also encompasses blood, spinal fluid, and other liquid sample of biologic origin, and may refer to either the cells or cell fragments suspended therein, or to the liquid medium and its solutes.

The term "relative amount" is used where a comparison is made between a test measurement and a control measurement. Thus, the relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

A "differential" result is generally obtained from an assay in which a comparison is made between the findings of two different assay samples, such as a cancerous cell line and a control cell line. Thus, for example, "differential expression" is observed when the level of expression of a particular gene is higher in one cell than another. "Differential display" refers to a display of a component, particularly RNA, from different cells to determine if there is a difference in the level of the component amongst different cells.

General Techniques

The practice of the present invention will employ, unless otherwise indicated, conventional techniques of molecular biology, microbiology, recombinant DNA, and immunology, which are within the skill of the art. Such techniques are explained fully in the literature. See, for example, "Molecular Cloning: A Laboratory Manual", Second Edition (Sambrook, Fritsch & Maniatis, 1989), "Oligonucleotide Synthesis" (M. J. Gait, ed., 1984), "Animal Cell Culture" (R. I. Freshney, ed., 1987); the series "Methods in Enzymology" (Academic Press, Inc.); "Handbook of Experimental Immunology" (D. M. Weir & C. C. Blackwell, Eds.), "Gene Transfer Vectors for Mammalian Cells" (J. M. Miller & M. P. Calos, eds., 1987), "Current Protocols in Molecular Biology" (F. M. Ausubel et al., eds., 1987); and "Current Protocols in Immunology" (J. E. Coligan et al., eds., 1991). All patents, patent applications, articles and publications mentioned herein, both supra and infra, are hereby incorporated herein by reference.

Features of the Cancer Gene Screening Method

The cancer gene screening method of this invention may be brought to bear to discover novel genes associated with cancer. The examples described below highlight its use in identifying four particular breast cancer genes, but the strategy can be applied to any cancer type of interest. It involves sequential application of different genetic techniques.

A central feature of the cancer gene screening method is to look for both DNA duplication and RNA overabundance relating to the same gene. This feature is particularly powerful in the discovery of new and potentially important cancer genes. While amplicons occur frequently in cancer, the presently available techniques indicate only the broad chromosomal region involved in the duplication event, not the specific genes involved. The present invention provides a way of detecting genes that may be present in an amplicon from a functional basis. Because an early part of the method involves detecting RNA, the method avoids genes that may be duplicated in an amplicon but are quiescent (and therefore irrelevant) in the cancer cells. Furthermore, it recruits active genes from a duplicated region of the chromosome too small to be detectable by the techniques used to describe amplicons.

The strategy for detecting such genes comprises a number of innovations over those that have been used in previous work.

The first part of the method is based on a search for particular RNAs that are overabundant in cancer cells. A first innovation of the method is to compare RNA abundance between control cells and several different cancer cells or cancer cell lines of the desired type. The cDNA fragments that emerge in a greater amount in several different cancer lines, but not in control cells, are more likely to reflect genes that are important in disease progression, rather than those that have undergone secondary or coincidental activation. It is particularly preferred to use cancer cells that are known to share a common duplicated chromosomal region.

A second innovation of this method is to supply as control, not RNA from a cell line or culture, but from fresh tissue samples of non-malignant origin. There are two reasons for this. First, the tissue will provide the spectrum of expression that is typical to the normal cell phenotype, rather than individual differences that may become more prominent in culture. This establishes a more reliable baseline for normal expression levels. More importantly, the tissue will be devoid of the effects that in vitro culturing may have in altering or selecting particular phenotypes. For example, proto-oncogenes or growth factors may become up-regulated in culture. When cultured cells are used as the control for differential display, these up-regulated genes would be missed.

A third innovation of this method is to undertake a subselection for cDNA corresponding to genes that achieve their RNA overabundance in a substantial proportion of cancer cells by gene duplication. To accomplish this, appropriate cDNA corresponding to overabundant RNA identified in the foregoing steps are used to probe digests of cellular DNA from a panel of different cancer cells, and from normal genomic DNA. cDNA that shows evidence of higher copy numbers in a proportion of the panel are selected for further characterization. An additional advantage of this step is that cDNA corresponding to mitochondrial genes can rapidly be screened away by including a mitochondrial DNA digest as an additional sample for testing the probe. This eliminates most of the false-positive cDNA, which otherwise make up a majority of the cDNA identified.

Thus, the identification of genes yielding products that are present at abnormal levels is accomplished by a method comprised of the following steps.

To identify particular RNA that is overabundant in cancer cells, RNA is prepared from both cancerous and control cells by standard techniques. Cancer-associated genes may affect cellular metabolism by any one of a number of mechanisms. For example, they may encode ribozymes, anti-sense polynucleotides, DNA-binding polynucleotides, altered ribosomal RNA, and the like. The gene screening methods of this invention may employ a comparison of RNA abundance levels at the total RNA level, not strictly limited to mRNA. However, the vast majority of cancer-associated genes are predicted to encode a protein gene whose up-regulation is closely linked to the metabolic process. For example, the four exemplary breast cancer genes described elsewhere in this application all comprise an open reading frame. Accordingly, a focus on mRNA enriches the selectable pool for candidate cancer-associated genes. Focus towards mRNA can be conducted at any step in the method. It is particularly convenient to use a display method that displays cDNA copied only from mRNA. In this case, whole RNA may be prepared and analyzed from cancer and control cell populations without separating out mRNA.

In terms of the cancer cells used as an RNA source, it is particularly advantageous to use a plurality of cancer cells known to contain a duplicated gene or chromosomal segment in the same region of the chromosome. The duplicated segment need not be the same size in all the cells, nor is it necessary that the number of duplications be the same, so long as there is at least some part of the duplicated segment that is shared amongst all the cancer cells used in the screen. Thus, a minimum of two, and preferably at least three cancer cells are used that are sufficiently characterized to identify a shared duplicated region, and can be used as a source of RNA for the screening test. In contrast, the control cell population will not comprise chromosomal duplications.

Assuming the duplication to be related to the malignancy of the cancer cells, RNA transcribed from the duplicated region is expected to be overabundant compared with that of the control cell. Accordingly, a highly effective strategy is to identify overabundant RNA that is present in all (or at least several) of the cancer cell preparations, but none of the control preparations. By using cancer cells that share a duplicated chromosomal region, the RNA comparison will be strongly biased in favor of RNA overabundance transcribed from the shared duplicated region. Since the shared region is optimally only a small segment of a single chromosome, expression differences arising from elsewhere in the genome in one cancer cell or another will not be selected. We have found that this is highly effective in eliminating: a) RNA abundance differences resulting from normal metabolic variations between cells; and/or b) RNA abundance differences related to cancer cell malignancy, but occurring secondarily to malignant transformation. This is important, because it considerably minimizes the chief deficiency in the use of RNA comparison methods, particularly differential display, for the screening of potential cancer genes: namely, the onerous number of false-positives that such techniques generate.

Shared duplicated regions in cancer cells may be identified by a relevant analytical technique, or by reference to such analysis already conducted and published. One approach that has been highly effective in mapping approximate sub-chromosomal locations of duplicated segments is comparative genotic hybridization (CGH). This technique involves extracting, amplifying and labeling DNA from the subject cell; hybridizing to reference metaphase chromosomes treated to remove repetitive sequences; and observing the position of the hybridized DNA on the chromosomes (WO 93/18186; Gray et al.). The greater the signal intensity at a given position, the greater the copy number of the sequences in the subject cell. Thus, regions showing elevated staining correspond to genes duplicated in the cancer cells, while regions showing diminished staining correspond to genes deleted in the cancer cells. Related techniques which a practitioner in the art will be well aware are methods for preparing and using repeat sequence chromosome-specific nucleic acid probes (U.S. Pat. No. 5,427,932; Weier et al.), methods for staining target chromosomal DNA using labeled nucleic acid fragments in conjunction with blocking fragments complementary to repetitive DNA segments (U.S. Pat. No. 5,447,841; Gray et al.), and methods for detecting amplified or deleted chromosomal regions using a mapped library of labeled polynucleotide probes (U.S. Pat. No. 5,472,842; Stokke et al.). If desired, multiple fluorochromes can be used as labeling agents with CGH and related techniques, to provide a three-color visualization of deleted, normal, and duplicated chromosome abnormalities (Lucas et al.).

The choice of a particular chromosomal mapping approach is irrelevant, especially once knowledge of the duplicated region is known. If the location of the chromosome duplication is already established for a cell line to be used in RNA comparison during the course of the present invention, then it is unnecessary to conduct a mapping technique de novo. For example, established cancer cell lines exist for which mapping data is already available in the public domain. Provided in the reference section of this application is a list of over 40 articles in which the locations of duplicated regions in particular cancer cells are described. In the context of the present invention, a plurality of cancer cells is chosen for the screening panel based on such data, so that they share a duplicated chromosomal region. The chromosomal location of a suspected duplication may be confirmed by hybridization analysis, if desired, using a probe specific for the location.

The cancer cells used for RNA comparison are also generally (but not necessarily) derived from the same type of cancer or the same tissue. Using cells derived from the same type of cancer increases the probability that the gene ultimately identified will be common in that type of cancer, and suitable as a type-specific diagnostic marker. Using cells derived from different types of cancer is in effect a search for cancer-related genes that are less tissue specific and more related to the malignant process in general. Both types of genes are of interest for both diagnostic and therapeutic purposes. In one illustration highlighted in Example 1, RNA was screened from the three breast cancer cell lines BT474, SKBR3, and MCF7, which have been determined by CGH or Southern analysis to share a duplicated genetic regions in chromosomes 1, 8, 14, 17, and 20. When the RNA from these cells was displayed, a number of RNA were found to be overabundant in the cancer cells, but not controls (FIG. 1). Three RNA overabundant in all three cancer cell lines corresponded to cancer-associated genes located on chromosomes 1, 8, and 14 that are listed in Table 1. The chromosome 13 gene (CH13-2a12-1) was overexpressed in 2 of the 3 cell lines; namely BT474 and SKBR3. Southern analysis subsequently established that the chromosome 13 gene was duplicated in the same two cell lines (Example 6, Table 5).

Selection of the source or sources of control cell RNA is also a matter of some refinement. The control RNA can be derived from in vitro cultures of non-malignant cells, or established cell lines derived from a non-malignant source. However, it is preferable for the control RNA to be obtained directly from normal human tissue of the same type as the cancer cells. This is because most normal cells do not proliferate indefinitely; hence adaptation of a cell into a cell line involves a degree of transformation. The transforming event may, in turn, be shared with that of certain cancer cells, at least at the level of RNA abundance. Hence, comparison of the RNA levels in cancer cells with so-called control cell lines may lead the practitioner to miss genes that are related to malignancy. For convenience, control cells may be maintained in culture for a brief period before the experiment, and even stimulated; however, multiple rounds of cell division are to be avoided if possible. Use of both stimulated and unstimulated cells as controls may help provide RNA patterns corresponding to the normal range of abundance within various metabolic events of the cell cycle. In one illustration highlighted in Example 1, RNA was screened using both proliferating and non-proliferating cells. As stated, the screening of breast cancer RNA is preferably conducted using uncultured normal mammary epithelial cells (termed "organoids") as sources of control RNA. These cells may be obtained from surgical samples resected from healthy breast tissue.

The RNA is preserved until use in the comparison experiment in such a way to minimize fragmentation. To facilitate confirmation experiments, it is useful to use RNA of a reproducible character. For this reason, it is convenient to use RNA that has been obtained from stable cancerous cell lines and/or ready tissue sources, although reproducibility can also be provided by preparing enough RNA so that it can be preserved in aliquots.

For displaying relative overabundance of RNA in the cancer cells, compared with the control cells, many standard techniques are suitable. These would include any form of subtractive hybridization or comparative analysis. Preferred are techniques in which more than two RNA sources are compared at the same time, such as various types of arbitrarily primed PCR fingerprinting techniques (Welsh et al., Yoshikawa et al.). Particularly preferred are differential mRNA display methods and variations thereof, in which the samples are run in neighboring lanes in a separating gel. These techniques are focused towards mRNA by using primers that are specific for the poly-A tail characteristic of mRNA (Liang et al., 1992a; U.S. Pat. No. 5,262,311).

Because many thousands of genes are expressed in the cells of higher organisms at any one time, it is preferable to improve the legibility of the display by surveying only a subset of the RNA at a time. Methods for accomplishing this are known in the art. A preferred method is by using selective primers that initiate PCR replication for a subset of the RNA. Thus, the RNA is first reverse transcribed by standard techniques. Short primers are used for the selection, preferably chosen such that alternative primers used in a series of like assays can complete a comprehensive survey of the mRNA.

In a preferred example, primers can be used for the 3' region of the mRNAs which have an oligo-dT sequence, followed by two other nucleotides (T$i$NM, where i≈11, N ∈ {A,C,G}, and M ∈ {A,C,G,T}). Thus, 12 possible primers are required to complete the survey. A random or arbitrary primer of minimal length can then be used for replication towards what corresponds in the sequence to the 5' region of the mRNA. The optimal length for the random primer is about 10 nucleotides. The product of the PCR reaction is labeled with a radioisotope, such as $^{35}$S. The labeled cDNA is then separated by molecular weight, such as on a polyacrylamide sequencing gel.

If desired, variations on the differential display technique may be employed. For example, one-base oligo-dT primers may be used (Liang et al., 1993 & 1994), although this is generally less preferred because the display pattern is correspondingly more complex. Selection of primers may be optimized mathematically depending on the number of RNA species in a tissue of interest (Bauer et al.). The method may be adapted for non-denaturing gels, and for use with automatic DNA sequencers (Bauer et al.). Alternative radioisotopes (Trentmann et al.) or fluorochromes (Sun et al.) may be used for labeling the differential display. Differential display may optionally be combined with a ribonuclease protection assay (Yeatman et al.). PCR primers may optionally incorporate a restriction site to facilitate cloning (Linskens et al., Ayala et al.). Using Taq polymerase from multiple manufacturers can increase the amount of variation under otherwise identical conditions (Haag et al.). Nested PCR primers may be used in differential display to decrease background created by oligo-dT primers (WO 95/33760). Other variants of the differential display technique are known in the art and described inter alia in the references cited in this disclosure. The use of such modifications are within the scope of the present invention, but are not required, as evidenced by the examples described below.

Based on the comparison of relative abundance of RNA, particular RNAs are chosen which are present as a higher proportion of the RNA in cancerous cells, compared with control cells. When using the differential display method, the cDNA corresponding to overabundant RNA will produce a band with greater proportional intensity amongst neighboring cDNA bands, compared with the proportional intensity in the control lanes. Desired cDNAs can be recovered most directly by cutting the spot in the gel corresponding to the band, and recovering the DNAs therefrom. Recovered cDNA can be replicated again for further use by any technique or combination of techniques known in the art, including PCR and cloning into a suitable carrier.

An optional but highly beneficial additional screening step, typically performed subsequently to an RNA comparison as described above, is aimed at identifying genes that are duplicated in a substantial proportion of cancers. This is conducted by using cDNA such as selected from differential display to probe digests of chromosomal DNA obtained from two or more cancerous cells, such as cancer cell lines. Chromosomal DNA from non-cancerous cells that essentially reflects the germ line in terms of gene copy number is used for the control. A preferred source of control DNA in experiments for human cancer genes is placental DNA, which is readily obtainable. The DNA samples are cleaved at sequence-specific sites along the chromosome, most usually with a suitable restriction enzyme into fragments of appropriate size. The DNA can be blotted directly onto a suitable medium, or separated on an agarose gel before blotting. The latter method is preferred, because it enables a comparison of the hybridizing chromosomal restriction fragment to determine whether the probe is binding to the same fragment in all samples. The amount of probe binding to DNA digests from each of the cancer cells is compared with the amount binding to control DNA.

Because the comparison is quantitative, it is preferable to standardize the measurement internally. One method is to administer a second probe to the same blot, probing for a second chromosomal gene unlikely to be duplicated in the cancer cells. This method is preferred, because it standardizes not only for differences in the amount of DNA provided, but also for differences in the amount transferred during blotting. This can be accomplished by using alternative labels for the two probes, or by stripping the first probe with a suitable eluant before administering the second.

To eliminate cDNA for mitochondrial genes, it is preferable to include in a parallel analysis a mitochondrial DNA preparation digested with the same restriction enzyme. Any cDNA probe that hybridizes to the appropriate mitochondrial restriction fragments can be suspected of corresponding to a mitochondrial gene.

In the initial replication of the RNA, the random primer may bind at any location along the RNA sequence. Thus, the copied and replicated segment may be a fragment of the full-length RNA. Longer cDNA corresponding to a greater portion of the sequence can be obtained, if desired, by several techniques known to practitioners of ordinary skill. These include using the cDNA fragment to isolate the corresponding RNA, or to isolate complementary DNA from a cDNA library of the same species. Preferably, the library is derived from the same tissue source, and more preferably from a cancer cell line of the same type. For example, for cDNA corresponding to human breast cancer genes, a preferred library is derived from breast cancer cell line BT474, constructed in lambda GT10.

Sequences of the cDNA can be determined by standard techniques, or by submitting the sample to commercial sequencing services. The chromosomal locations of the genes can be determined by any one of several methods known in the art, such as in situ hybridization using chromosomal smears, or panels of somatic cell hybrids of known chromosomal composition.

The cDNA obtained through the selection process outlined can then be tested against a larger panel of cancer cell lines and/or fresh tumor cells to determine what proportion of the cells have duplicated the gene. This can be accomplished by using the cDNA as a probe for chromosomal DNA digests, as described earlier. As illustrated in the Example section, a preferred method for conducting this determination is Southern analysis.

The cDNA can also be used to determine what proportion of the cells have RNA overabundance. This can be accomplished by standard techniques, such as slot blots or blots of agarose gels, using whole RNA or messenger RNA from each of the cells in the panel. The blots are then probed with the cDNA using standard techniques. It is preferable to provide an internal loading and blotting control for this analysis. A preferred method is to re-probe the same blot for transcripts of a gene likely to be present in about the same level in all cells of the same type, such as the gene for a cytoskeletal protein. Thus, a preferred second probe is the cDNA for beta-actin.

Using a novel cDNA found by this selection procedure, it is anticipated that essentially all cancer cells showing gene duplication will also show RNA overabundance, but that some will show RNA overabundance without gene duplication.

The practitioner will readily appreciate that the strategies for identifying genes that are duplicated and/or associated with RNA overabundance may be reversed appropriately to screen for genes that are deleted and/or associated with RNA underabundance. The principles are essentially the same.

Genes that are frequently down-regulated in cancer (such as tumor suppresser genes) may be down-regulated by different mechanisms in different cells, and a gene with this behavior is more likely to be central to malignant transformation or persistence of the malignant state.

To screen for such down-regulated genes according to the present invention, RNA is prepared from a plurality of tumors or cancer cell lines and the abundance is compared with RNA preparation from control cells. Again, it is highly preferable to use cancer cells that share a deleted gene in the same chromosomal region, in order to focus any differences at the RNA level towards particular alterations in cancer cells and away from normal variations or coincidental changes. The CGH technique may be used to identify deletions in previously uncharacterized cancer cells. As before, cancer cells may be chosen on the basis of previous knowledge of deleted regions; there is no need to conduct methods such as CGH on previously characterized lines. cDNA from the RNA of cancer cells is displayed (preferably by differential display) alongside cDNA copied from (preferably uncultured) control cells, and cDNA is selected that appears to be underrepresented in at least two (preferably more) of the cancer cells compared with the control cells. cDNA thus selected may optionally be further screened against digested DNA preparations, to confirm that the RNA underabundance observed in the cancer cell populations is attributable in at least a proportion of the cells to an actual gene deletion.

As before, the cDNA may be used for sequencing or rescuing additional polynucleotides, in this case not from the cancer cells but from cells containing or expressing the gene at normal levels. Pharmaceuticals based on deleted genes or those associated with underexpressed RNA are typically oriented at restoring or upregulating the gene, or a functional equivalent of the encoded gene product.

Further Characterization and Use of Identified Cancer Gene Sequences

Any cDNA selected by the strategy just outlined (for example, those corresponding to the breast cancer genes highlighted in the Example section) can be replicated to provide a larger supply by any standard technique, such as PCR or gene cloning. Alternatively, the cDNA can be sequenced, and the sequence data can be used to produce a polynucleotide by artificial synthesis that is identical in sequence, or that incorporates occasional variations. Devices are commercially available that perform the synthesis reactions automatically.

Polypeptides encoded by the corresponding mRNA can be prepared by several different methods, all of which will be known to a practitioner of ordinary skill. For example, the appropriate strand of the full-length cDNA can be operatively linked to a suitable promoter, and transfected into a suitable host cell. The host cell is then cultured under conditions that allow transcription and translation to occur, and the polypeptide is subsequently recovered. Another convenient method is to determine the polynucleotide sequence of the cDNA, and predict the polypeptide sequence according to the genetic code. A polypeptide can then be prepared directly, for example, by chemical synthesis, either identical to the predicted sequence, or incorporating occasional variations.

Monoclonal and polyclonal antibodies against polypeptides encoded by cancer genes may be prepared by injecting the suitably prepared polypeptide into an experimental animal. Sera harvested from immunized animals provide a source of polyclonal antibodies. Unwanted activity cross-reacting with other antigens, if present, can be removed by standard techniques, and the specific antibody activity can be further purified. Alternatively, immune cells such as splenocytes can be recovered from the immunized animals and used to prepare a monoclonal antibody-producing cell line. See, for example, Harrow & Lane (1988). Briefly, an antibody-producing line is typically produced by cell fusion, or by transfecting antibody-producing cells with Epstein Barr Virus. The treated cells are cloned and cultured, and clones are selected that produce antibody of the desired specificity, for example, in a standard immunoassay. A supply of monoclonal antibody from the selected clones can be purified from tissue culture supernatant, or from ascites fluid. Antibody fragments and other derivatives can be prepared by methods of standard protein chemistry, such as subjecting the antibody to cleavage with a proteolytic enzyme. Genetically engineered variants of the antibody can be produced by applying the general methods of molecular biology.

Novel cDNA sequences corresponding to genes associated with cancer are potentially useful as diagnostic aids. Similarly, polypeptides encoded by such genes, and antibodies specific for these polypeptides, are also potentially useful as diagnostic aids. Gene duplication or overabundance of RNA in particular cells can help identify those cells as being cancerous, and thereby play a part in the initial diagnosis. For patients already diagnosed with cancer, gene duplication or overabundance of RNA can assist with clinical management and prognosis. For example, overabundance of RNA may be a useful predictor of disease survival, metastasis, susceptibility to various regimens of standard chemotherapy, the stage of the cancer, or its aggressiveness. See generally the article by Blast, U.S. Pat. No. 4,968,603 (Slamon et al.) and PCT application WO 94/00601 (Levine et al.). All of these determinations are important in helping the clinician choose between the available treatment options. A particularly important diagnostic application contemplated in this invention is the identification of patients suitable for gene-specific therapy. For example, treatment directed against a particular gene or gene product is appropriate in cancers where the gene is duplicated or there is RNA overabundance.

The polynucleotide, polypeptide, and antibodies developed from genes identified by this invention may be used as reagents in standard diagnostic procedures. For example, polynucleotides can be used as reagents to detect a DNA or RNA target, such as might be present in a cell with duplication or RNA overabundance of the corresponding gene. Polypeptides can be used as reagents to detect a target for which it has a specific binding site, such as an antibody molecule or (if the polypeptide is a receptor) the corresponding ligand. Antibodies can be used as reagents to detect a target it specifically recognizes, such as the polypeptide used as an immunogen to raise it.

The target is supplied by obtaining a suitable tissue sample from individuals suspected of containing cancerous cells of the appropriate type. The reaction is performed by contacting the reagent with the sample under conditions that will allow a complex to form between the reagent and the target. The reaction may be performed in solution, or on a solid tissue sample, for example, using histology sections. Formation of the complex is detected by a number of techniques known in the art. For example, the reagent may be supplied with a label and unreacted reagent may be removed from the complex; the amount of remaining label thereby indicating the amount of complex formed. To determine whether the amount of complex formed is representative of cancerous or non-cancerous cells, the assay result is compared with a similar assay conducted on a suitable control sample.

A polynucleotide corresponding to a cancer associated gene can be used as a reagent for determining gene duplication or RNA overabundance that may be present in a clinical sample. The binding of the reagent polynucleotide to a target in a clinical sample generally relies in part on a hybridization reaction between a region of the polynucleotide reagent, and the DNA or RNA in a sample being tested. To measure gene duplication, the preparation is preferably enriched for chromosomal DNA; to measure RNA overabundance, the preparation is preferably enriched for RNA. Hybridization is allowed to occur by mixing the reagent polynucleotide with a sample suspected of containing a target polynucleotide under appropriate reaction conditions; generally where both target and reagent are at least partly equilibrated into the single-stranded form. In order to detect the complexes formed between the reagent and the target, the reagent is generally provided with a label, such as $^{32}$P, fluorescein, or alkaline phosphatase. The target and/or the reagent may optionally be replicated during the test, or branched polynucleotides can be used to increase reaction sensitivity.

An antibody can also be used as a reagent in cancer diagnosis, or for determining gene duplication or RNA overabundance that may be present in a clinical sample. This relies on the fact that overabundance of RNA in affected cells is often associated with increased production of the corresponding polypeptide. Several of the genes up-regulated in cancer cells encode for cell surface receptors—for example, erbB-2, c-myc and epidermal growth factor. Alternatively, the RNA may encode a protein kept inside the cell, or it may encode a protein secreted by the cell into the surrounding milieu. Any such protein product can be detected in solid tissue samples and cultured cells by standard immunohistological techniques. The amount of protein corresponding to the cancer-associated gene may also be detected in a standard quantitative immunoassay of plasma or serum samples, and solubilized tissue samples.

A polypeptide encoded by an identified cancer gene can also be used as a reagent in cancer diagnosis. Overabundance of RNA in affected cells may result in the corresponding polypeptide being produced by the cells in an abnormal amount, or expression of the polypeptide in an unusual form. This in turn may result in stimulation of the immune response of the host to produce its own antibody molecules that are specific for the polypeptide. Accordingly, the polypeptide may be used for the detection of such antibodies in a subject suspected of having cancer, such as by conducting an immunoassay.

Also contemplated in this invention are modes of treating subjects bearing cancer cells that have overabundance of the particular RNA described. The strategy used to obtain the cDNAs provided in this invention was deliberately focused on genes that achieve RNA overabundance by gene duplication in some cells, and by alternative mechanisms in other cells. These alternative mechanisms may include, for example, translocation or enhancement of transcription enhancing elements near the coding region of the gene, deletion of repressor binding sites, or altered production of gene regulators. Such mechanisms would result in more RNA being transcribed from the same gene. Alternatively, the same amount of RNA may be transcribed, but may persist longer in the cell, resulting in greater abundance. This could occur, for example, by reduction in the level of ribozymes or protein enzymes that degrade RNA, or in the modification of the RNA to render it more resistant to such enzymes or spontaneous degradation.

Thus, different cells make use of at least two different mechanisms to achieve a single result—the overabundance of a particular RNA. This suggests that RNA overabundance of these genes is central to the cancer process in the affected cells. Interfering with the specific gene or gene product would consequently modify the cancer process. It is an objective of this invention to provide pharmaceutical compositions that enable therapy of this kind.

One way this invention achieves this objective is by the use of identified cancer genes for screening candidate drugs. The general screening strategy is to apply the candidate to a manifestation of a gene associated with cancer, and then determine whether the effect is beneficial and specific. For example, a composition that interferes with a polynucleotide or polypeptide corresponding any of the novel cancer-associated genes described herein has the potential to block the associated pathology when administered to a tumor of the appropriate phenotype. It is not necessary that the mechanism of interference be known; only that the interference be preferential for cancerous cells (or cells near the cancer site) but not other cells.

A preferred method of screening is to provide cells in which a polynucleotide related to a cancer gene has been transfected. See, for example, PCT application WO 93/08701. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element.

A cell line is chosen which has a phenotype desirable in testing, and which can be maintained well in culture. The cell line is transfected with a polynucleotide corresponding to one of the cancer-associated genes identified herein. Transfection is performed such that the polynucleotide is operatively linked to a genetic controlling element that permits the correct strand of the polynucleotide to be transcribed within the cell. Successful transfection can be determined by the increased abundance of the RNA compared with an untransfected cell. It is not necessary that the cell previously be devoid of the RNA, only that the transfection result in a substantial increase in the level observed. RNA abundance in the cell is measured using the same polynucleotide, according to the hybridization assays outlined earlier.

Drug screening is performed by adding each candidate to a sample of transfected cells, and monitoring the effect. The experiment includes a parallel sample which does not receive the candidate drug. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, and the ability of the cells to interact with other cells or compounds. Differences between treated and untreated cells indicates effects attributable to the candidate. In a preferred method, the effect of the drug on the cell transfected with the polynucleotide is also compared with the effect on a control cell. Suitable control cells include untransfected cells of similar ancestry, cells transfected with an alternative polynucleotide, or cells transfected with the same polynucleotide in an inoperative fashion. Optimally, the drug has a greater effect on operatively transfected cells than on control cells.

Desirable effects of a candidate drug include an effect on any phenotype that was conferred by transfection of the cell line with the polynucleotide from the cancer-associated gene, or an effect that could limit a pathological feature of the gene in a cancerous cell. Examples of the first type would be a drug that limits the overabundance of RNA in the transfected cell, limits production of the encoded protein, or limits the functional effect of the protein. The effect of the drug would be apparent when comparing results between treated and untreated cells. An example of the second type would be a drug that makes use of the transfected gene or a gene product to specifically poison the cell. The effect of the drug would be apparent when comparing results between operatively transfected cells and control cells.

This invention also contemplates gene-specific pharmaceuticals in which polynucleotides, polypeptides, and antibodies corresponding to a cancer gene are specific active ingredient in pharmaceutical compositions. Such compositions may decrease the pathology of cancer cells on their own, or render the cancer cells more susceptible to treatment by the non-specific agents, such as classical chemotherapy or radiation.

An example of how polynucleotides embodied in this invention can be effectively used in treatment is gene therapy. The general principle is to introduce the polynucleotide into a cancer cell in a patient, and allow it to interfere with the expression of the corresponding gene. A preferred mode of gene therapy is to provide the polynucleotide in such a way that it will replicate inside the cell, enhancing and prolonging the interference effect, by providing the polynucleotide operatively linked to a suitable promoter.

The use of antibodies in the treatment of cancer partly relies on the fact that genes that show RNA overabundance in cancer frequently encode cell-surface proteins. Location of these proteins at the cell surface may correspond to an important biological function of the cancer cell, such as their interaction with other cells, the modulation of other cell-surface proteins, or triggering by an incoming cytokine. For example, if the gene encodes for a growth receptor, then an antibody that blocks the ligand binding site or causes endocytosis of the receptor would decrease the ability of the receptor to provide its signal to the cell. The effectiveness of a particular antibody can be predicted empirically by testing with cultured cancer cells expressing the corresponding protein. Another example of how antibodies can be used in cancer therapy is in the specific targeting of effector components towards the protein product of the cancer-associated gene on cancer cells. Suitable effector components in such compositions include radionuclides such as $^{131}$I, toxic chemicals such as vincristine, toxic peptides such as diphtheria toxin, effector peptides or polynucleotides capable, for example, of installing a tumor suppresser gene, or rendering cancer cells susceptible to immune attack.

An example of how polypeptides encoded by cancer genes can be effectively used in treatment is through vaccination. The growth of cancer cells is naturally limited in part due to immune surveillance. Stimulation of the immune system using a particular tumor-specific antigen enhances the effect towards the tumor expressing the antigen. An active vaccine comprising a polypeptide encoded by the cDNA of this invention would be appropriately administered to subjects having overabundance of the corresponding RNA, or those predisposed for developing cancer cells with overabundance of the same RNA. Polypeptide antigens are typically combined with an adjuvant such as DETOX™ as part of a vaccine composition. The vaccine is preferably administered first as a priming dose, and then again as a

Example 1

Selecting cDNA for Messenger RNA that is Overabundant in Breast Cancer Cells Total RNA was isolated from each breast cancer cell line or control cell by centrifugation through a gradient of guanidine isothiocyanate/CsCl. The RNA was treated with RNase-free DNase (Promega, Madison, Wis.). After extraction with phenol-chloroform, the RNA preparations were stored at −70° C. Oligo-dT polynucleotides for priming at the 3' end of messenger RNA with the sequence $T_{11}NM$ (where $N \in \{A,C,G\}$ and $M \in \{A,C,G,T\}$) were synthesized according to standard protocols. Arbitrary decamer polynucleotides (OPA01 to OPA20) for priming towards the 5' end were purchased from Operon Biotechnology, Inc., Alameda, Calif.

The RNA was reverse-transcribed using AMV reverse transcriptase (obtained from BRL) and an anchored oligo-dT primer in a volume of 20 μL, according to the manufacturer's directions. The reaction was incubated at 37° C. for 60 min and stopped by incubating at 95° C. for 5 min. The cDNA obtained was used immediately or stored frozen at −70° C.

Differential display was conducted according to the following procedure: 1 μL cDNA was replicated in a total volume of 10 μL PCR mixture containing the appropriate $T_{11}NM$ sequence, 0.5 μM of a decamer primer, 200 μM dNTP, 5 μCi [$^{35}$S]-dATP (Amersham), Taq polymerase buffer with 2.5 mM $MgCl_2$ and 0.3 unit Taq polymerase (Promega). Forty cycles were conducted in the following sequence: 94° C. for 30 sec, 40° C. for 2 min, 72° C. for 30 sec; and then the sample was incubated at 72° C. for 5 min. The replicated cDNA was separated on a 6% polyacrylamide sequencing gel. After electrophoresis, the gel was dried and exposed to X-ray film.

The autoradiogram was analyzed for labeled cDNA that was present in larger relative amount in all of the lanes corresponding to breast cancer cells, compared with all of the lanes corresponding to control cells. FIG. 1 provides an example of an autoradiogram from such an experiment. Lane 1 is from non-proliferating normal breast cells; lane 2 is from proliferating normal breast cells; lanes 3 to 5 are from breast cancer cell lines BT474, SKBR3, and MCF7. The left and right side shows the pattern obtained from experiments using the same $T_{11}NM$ sequence ($T_{11}AC$), but two different decamer primers. The arrows indicate the cDNA fragments that were more abundant in all three tumor lines compared with controls.

The assay illustrated in FIG. 1 was conducted using different combinations of oligo-dT primers and decamer primers. A number of differentially expressed bands were detected when different primer combinations were used. However, not all differences seen initially were reproducible after re-screening. We therefore routinely repeated each differential display for each primer combination. Only bands showing RNA overabundance in at least 2 experiments were selected for further analysis.

It is preferable to include in the differential display experiment RNA derived from uncultured normal mammary epithelial cells (termed "organoids"). These cells are obtained from surgical samples resected from healthy breast tissue, which are then coaxed apart by blunt dissection techniques and mild enzyme treatment. Using organoids as the negative control, 33 cDNA fragments were isolated from 15 displays.

Example 2

Sub-selecting cDNA that Corresponds to Genes that are Duplicated in Breast Cancer Cells cDNA fragments that were differentially expressed in the fashion described in Example 1 were excised from the dried gel and extracted by boiling at 95° C. for 10 min. Eluted cDNA was recovered by ethanol precipitation, and replicated by PCR. The product was cloned into the pCRII vector using the TA cloning system (Invitrogen).

EcoRI digested placenta DNA, and EcoRI digested DNA from the breast cancer cell lines BT474, SKBR3 and ZR-75-30 were used to prepare Southern blots to screen the cloned cDNA fragments. The cloned cDNA fragments were labeled with [32P]-dCTP, and used individually to probe the blots. A larger relative amount of binding of the probe to the lanes corresponding to the cancer cell DNA indicated that the corresponding gene had been duplicated in the cancer cells. The labeled cDNA probes were also used in Northern blots to verify that the corresponding RNA was overabundant in the appropriate cell lines. To determine whether the cDNA fragments obtained by this selection procedure corresponded to novel genes, a partial nucleotide sequence was obtained using M13 primers. Each sequence was compared with the known sequences in GenBank. In initial experiments, 5 of the first 7 genes sequenced were mitochondrial genes. To avoid repeated isolation of mitochondrial genes, subsequent screening experiments were done with additional lanes in the DNA blot analysis for EcoRI digested and HindIII digested mitochondrial DNA. Any cDNA fragment that hybridized to the appropriate mitochondrial restriction fragments was suspected of corresponding to a mitochondrial gene, and not analyzed further.

From the 33 cDNA fragments detected from differential displays using organoid mRNA, 12 were subcloned. Of these 12, 6 detected suitable gene duplications in the appropriate cell lines. Three cDNA failed to detect duplicated genes, and 3 appeared to correspond to mitochondrial genes. Sequence analysis of the 6 suitable cDNA fragments showed no identity to any known genes.

To obtain longer cDNA corresponding to the cDNA fragments with novel sequences, the fragments were used as probes to screen a cDNA library from breast cancer cell line BT474, constructed in lambda GT10. The longer cDNA obtained from lambda GT10 were sequenced using lambda GT10 primers. The chromosomal locations of the cDNAs were determined using panels of somatic cell hybrids.

Four of the 6 novel cDNA identified so far have been processed in this fashion. The probes used to obtain the 4 new breast cancer genes are shown in Table 2.

TABLE 2

| Primers used for Differential Display | | |
|---|---|---|
| cDNA | Oligo-dT primer | Arbitrary primer |
| CH1-9a11-2 | $T_{11}CC$ (SEQ ID NO: 9) | SEQ ID NO: 11 |
| CH8-2a13-1 | $T_{11}AC$ (SEQ ID NO: 10) | SEQ ID NO: 12 |
| CH13-2a12-1 | $T_{11}AC$ (SEQ ID NO: 10) | SEQ ID NO: 13 |
| CH14-2a16-1 | $T_{11}AC$ (SEQ ID NO: 10) | SEQ ID NO: 14 |

Example 3

Using the cDNA to Test Panels of Breast Cancer Cells

To determine the proportion of breast cancers in which the putative breast cancer genes were duplicated, or showed RNA overabundance without gene duplication, the four cDNA obtained according to the selection procedures described were used to probe a panel of breast cancer cell lines and primary tumors.

Gene duplication was detected either by Southern analysis or slot-blot analysis. For Southern analysis, 10 μg of EcoRI digested genomic DNA from different cell lines was electrophoresed on 0.8% agarose and transferred to a HYBOND™ N+membrane (Amersham). The filters were hybridized with 32P-labeled cDNA for the putative breast cancer gene. After an autoradiogram was obtained, the probe was stripped and the blot was re-probed using a reference probe to adjust for differences in sample loading. Either chromosome 2 probe D2S5 or chromosome 21 probe D21S6 was used as a reference. Densities of the signals on the autoradiograms were obtained using a densitometer (Molecular Dynamics). The density ratio between the breast cancer gene and the reference gene was calculated for each sample. Two samples of placental DNA digests were run in each Southern analysis as a control.

For slot-blot analysis, 1 μg of genomic DNA was denatured and slotted on the HYBOND™ membrane. D21S5 or human repetitive sequences were used as reference probes for slot blots. The density ratio between the breast cancer gene and the reference gene was calculated for each sample. 10–15 samples of placental DNA digests were used as control.

Amongst the control samples, the highest density ratio was set at 1.0. The density ratio of the tumor cell lines were standardized accordingly. An arbitrary cut-off for the standardized ratio (typically 1.3) was defined to identify samples in which the putative gene had been duplicated. Each of the cell lines in the breast cancer panel was scored positively or negatively for duplication of the gene being tested.

Some of the cell lines in the panel were known to have duplicated chromosomal regions from comparative genomic hybridization analysis. In instances where the cDNA being used as probe mapped to the known amplified region, the cDNA indicated that the corresponding gene had also been duplicated. However, duplicated genes were also detected using each of the four cDNAs in instances where comparative genomic hybridization had not revealed any amplification.

Because of the nature of the technique, the standardized ratio calculated as described underestimates the gene copy number, although it is expected to rank in the same order. For example, the standardized ratio obtained for the c-myc gene in the SKBR3 breast cancer cell was 5.0. However, it is known that SKBR3 has approximately 50 copies of the c-myc gene.

To test for overabundance of RNA, 10 μg of total RNA from breast cancer cell lines or primary breast cancer tumors were electrophoresed on 0.8% agarose in the presence of the denaturant formamide, and then transferred to a nylon membrane. The membrane was probed first with 32P-labeled cDNA corresponding to the putative breast cancer gene, then stripped and reprobed with 32P-labeled cDNA for the beta-actin gene to adjust for differences in sample loading. Ratios of densities between the candidate gene and the beta-actin gene were calculated. RNA from three different cultured normal epithelial cells were included in the analysis as a control for the normal level of gene expression. The highest ratio obtained from the normal cell samples was set at 1.0, and the ratios in the various tumor cells were standardized accordingly.

Example 4

Chromosome 1 Gene CH1-9a11-2

One of the cDNA obtained through the selection procedures of Examples 1 and 2 corresponded to a gene that mapped to Chromosome 1.

Table 3 summarizes the results of the analysis for gene duplication and RNA overabundance. Both quantitative and qualitative assessment is shown. The numbers shown were obtained by comparing the autoradiograph intensity of the hybridizing band in each sample with that of the controls. Several control samples were used for the gene duplication experiments, consisting of different preparations of placental DNA. The control sample with the highest level of intensity was used for standardizing the other values. Other sources used for this analysis were breast cancer cell lines with the designations shown. For reasons stated in Example 3, the quantitative number is not a direct indication of the gene copy number, although it is expected to rank in the same order. Similarly, up to 6 control samples were used for the RNA overabundance experiments, consisting of different preparations of breast cell organoids which had been maintained briefly in tissue culture until the experiment was performed. The control sample with the highest level of intensity was used for standardizing the other values. Each cell line was scored + or − according to an arbitrary cut-off value.

TABLE 3

Chromosome 1 Gene in Breast Cancer Cell Lines

| Source | CH1-9a11-2 Gene Duplication | | CH1-9a11-2 RNA Overabundance | | | |
|---|---|---|---|---|---|---|
| | | | 5.2kb | | 4.4kb | |
| Normal | − | 1.00* | − | 1.00** | − | 1.0** |
| BT474 | + | 2.70 | + | 1.57 | + | 3.7 |
| ZR-75-30 | + | 2.65 | | nd | | nd |
| MDA453 | + | 2.86 | + | 5.79 | + | 6.2 |
| MDA435 | + | 3.72 | − | 0.89 | + | 2.4 |
| SKBR3 | + | 1.86 | − | 0.94 | + | 2.9 |
| 600PE | + | 1.72 | + | 4.47 | + | 6.8 |
| MDA157 | + | 1.49 | − | 1.08 | + | 1.4 |
| MCF7 | + | 1.95 | | nd | | nd |
| DU4475 | + | 2.02 | − | 1.13 | + | 1.5 |
| MDA231 | − | 1.23 | + | 1.47 | − | |
| BT20 | − | 1.09 | − | 0.83 | + | 1.9 |
| T47D | − | 1.05 | | nd | | nd |
| UACC812 | − | 0.67 | + | 1.57 | + | 1.8 |
| MDA134 | − | 1.19 | + | 5.04 | + | 7.1 |
| CAMA-1 | − | 1.02 | + | 2.51 | + | 7.2 |

TABLE 3-continued

Chromosome 1 Gene in Breast Cancer Cell Lines

| Source | CH1-9a11-2 Gene Duplication | CH1-9a11-2 RNA Overabundance 5.2kb | 4.4kb |
|---|---|---|---|
| Incidence (%) | 9/15 (60%) | 7/12 (58%) | 11/12 (92%) |

Gene duplication or RNA overabundance; - no duplication or overabundance; nd = not done
*Degree of gene duplication is reported relative to placental DNA preparations.
**Degree of RNA overabundance is reported relative to the highest level observed for several cultures of normal epithelial cells. Two hybridizing species of RNA are calculated and reported separately.

The gene corresponding to the CH1-9a11-2 cDNA was duplicated in 9 out of 15 (60%) of the breast cancer cell lines tested, compared with placental DNA digests (P3 and P12). The sequence of the 115 bases from the 5' end of the cDNA fragment is listed in FIG. 6 (SEQ ID NO:1), and showed no homology to any known gene in GenBank. One of the three possible reading frames was found to be open, with the predicted amino acid sequence of SEQ ID NO:2.

Example 5

Chromosome 8 gene CH8-2a13-1

Figure 2:
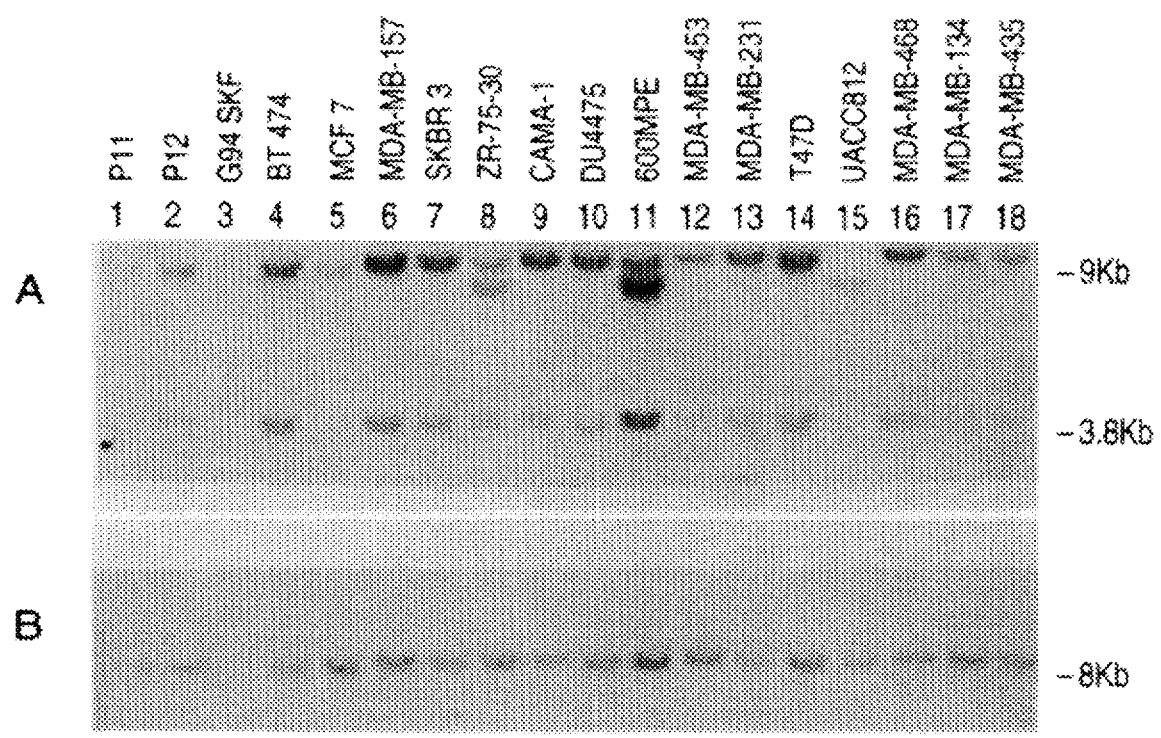
FIG. 2 is a half-tone reproduction of an autoradiogram of electrophoresed DNA digests from a panel of breast cancer cell lines probed with CH8-2a13-1 (Panel A) or a loading control (Panel B).

One of the cDNA obtained corresponded to a gene that mapped to Chromosome 8. FIG. 2 shows the Southern blot analysis for the corresponding gene in various DNA digests. Lane 1 (P12) is the control preparation of placental DNA; the rest show DNA obtained from human breast cancer cell lines. Panel A shows the pattern obtained using the 32P-labeled CH8-2a13-1 cDNA probe. Panel B shows the pattern obtained with the same blot using the 32P-labeled D2S6 probe as a loading control. The sizes of the restriction fragments are indicated on the right.

Figure 3:
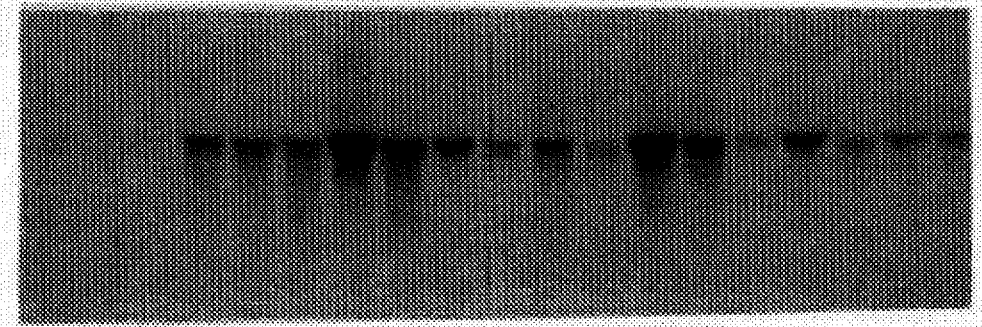
FIG. 3 is a half-tone reproduction of an autoradiogram of electrophoresed total RNA from a panel of breast cancer cell lines probed with CH8-2a13-1 (Panel A) or a loading control (Panel B).
Figure 3:
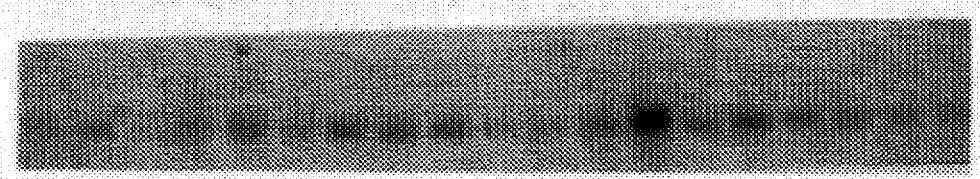

FIG. 3 shows the Northern blot analysis for RNA overabundance. Lanes 1–3 show the level of expression in cultured normal epithelial cells. Lanes 4–19 show the level of expression in human breast cancer cell lines. Panel A shows the pattern obtained using the CH8-2a13-1 probe; panel B shows the pattern obtained with beta-actin cDNA, a loading control.

The results are summarized in Table 4. The scoring method is the same as for Example 4. The gene corresponding to CH8-2a13-1 showed clear evidence of duplication in 12 out of 17 (71%) of the cells tested. RNA overabundance was observed in 14 out of 17 (82%). Thus, 11% of the cells had achieved RNA overabundance by a mechanism other than gene duplication.

Since the known oncogene c-myc is located on Chromosome 8, the Southern analysis was also conducted using a probe for c-myc. At least 2 of the breast cancer cells showing duplication of the gene corresponding to CH8-2a13-1 gene did not show duplication of c-myc. This indicates that the gene corresponding to CH8-2a13-1 is not part of the myc amplicon.

The sequence of 150 bases from the 5' end of the cDNA fragment is listed in FIG. 6 (SEQ ID NO:3), and showed no homology to any known gene in GenBank. One of the three possible reading frames was found to be open, with the amino acid sequence of SEQ ID NO:4.

TABLE 4

Chromosome 8 Genes in Breast Cancer Cell Lines

| Source | CH8-2a13-1 Gene Duplication | | CH8-2a13-1 RNA Overabundance | | c-myc Gene Duplication | |
|---|---|---|---|---|---|---|
| Normal | – | 1.00* | – | 1.00** | – | 1.00* |
| SKBR3 | + | 4.25 | + | 4.30 | + | 4.73 |
| ZR-75-30 | + | 3.82 | nd | | + | 2.24 |
| BT474 | + | 1.53 | + | 1.72 | + | 1.76 |
| MDA157 | + | 2.02 | + | 3.39 | + | 1.39 |
| MCF7 | + | 1.84 | + | 4.92 | + | 3.10 |
| CAMA-1 | + | 3.62 | + | 2.14 | + | 1.61 |
| MDA361 | + | 2.00 | + | 1.74 | nd | |
| MDA468 | nd | | + | 4.50 | nd | |
| T47D | + | 1.41 | + | 1.58 | – | 1.02 |
| MDA453 | + | 1.83 | + | 3.10 | – | 0.90 |
| MDA134 | + | 1.30 | + | 3.70 | – | 0.88 |
| MDA435 | + | 2.15 | + | 4.94 | – | 1.00 |
| 600PE | – | 0.95 | + | 2.04 | – | 0.54 |
| UACC812 | + | 1.25 | + | 2.40 | – | 0.74 |
| MDA231 | – | 0.80 | + | 1.28 | + | 1.27 |
| DU4475 | – | 0.85 | – | 0.88 | – | 0.50 |
| BT468 | – | 0.37 | – | 0.70 | – | 0.23 |
| BT20 | – | 0.95 | – | 0.82 | – | |
| Incidence (%) | 12/17 (71%) | | 14/17 (82%) | | 71/6 (44%) | |

+ Gene duplication or RNA overabundance; - no duplication or overabundance; nd = not done.
*Degree of gene duplication is reported relative to placental DNA preparations.
**Degree of RNA overabundance is reported relative to the highest level observed for several cultures of normal epithelial cells.

Example 6

Chromosome 13 Gene CH13-2a12-1

Figure 4:
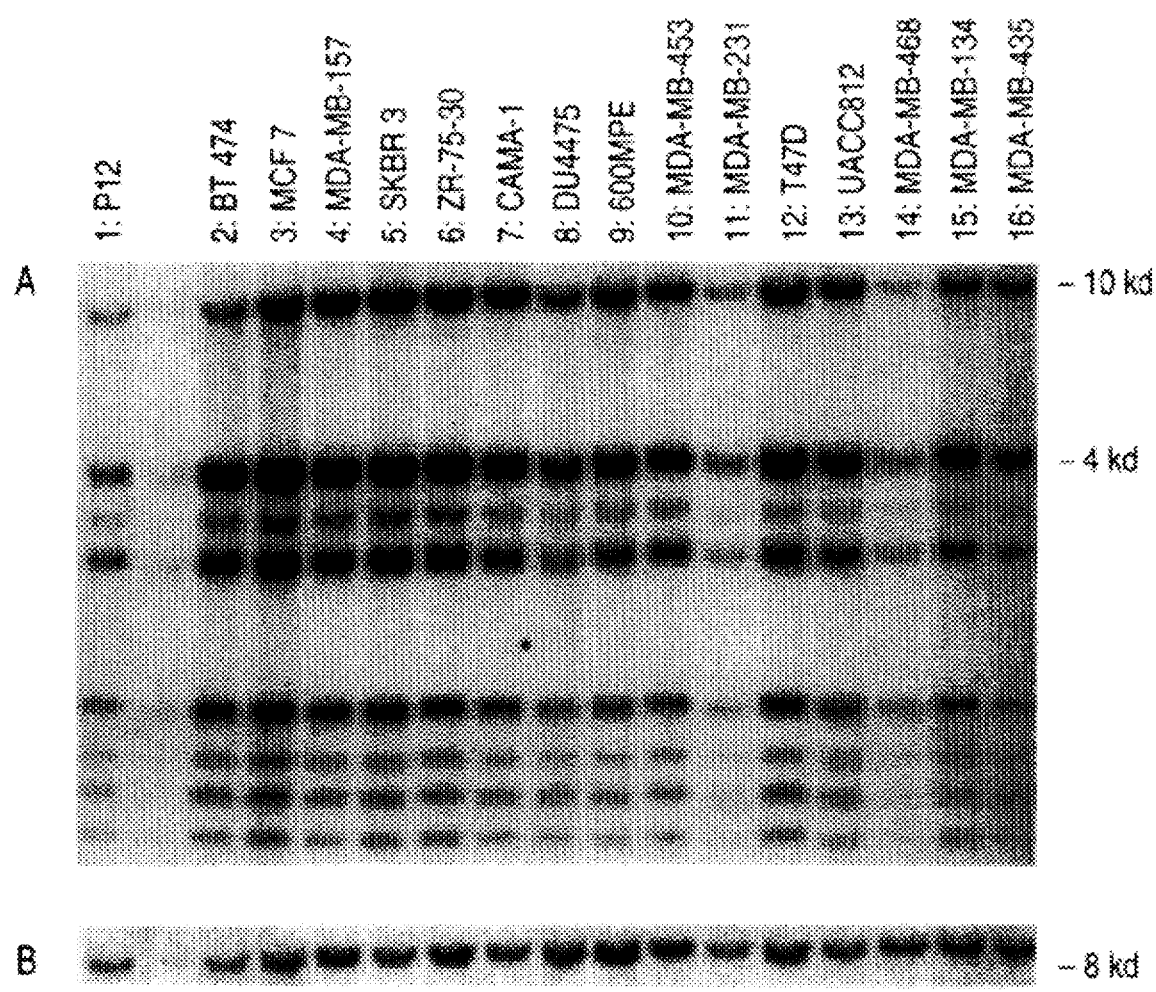
FIG. 4 is a half-tone reproduction of an autoradiogram of electrophoresed DNA digests from a panel of breast cancer cell lines probed with CH13-2a12-1.

One of the cDNA obtained corresponded to a gene that mapped to Chromosome 13. FIG. 4 shows the Southern blot analysis for the corresponding gene in various DNA digests. Lanes 1 and 2 are control preparations of placental DNA; the rest show DNA obtained from human breast cancer cell lines. Panel A shows the pattern obtained using the CH13-2a12-1 cDNA probe; panel B shows the pattern using D2S6 probe as a loading control. The sizes of the restriction fragments are indicated on the right.

Figure 5:
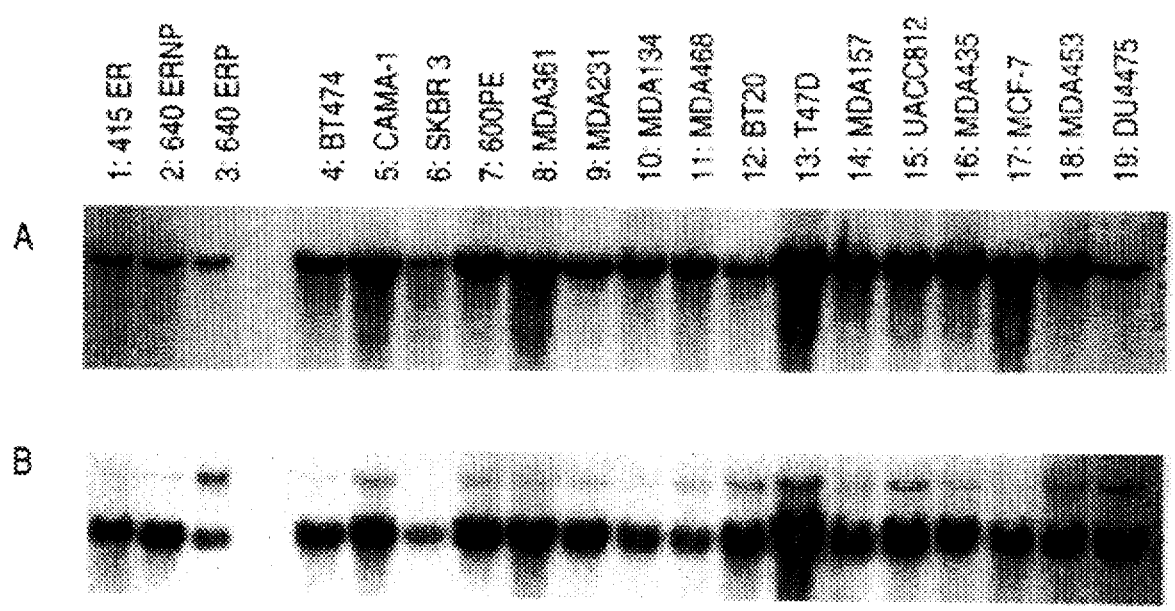
FIG. 5 is a half-tone reproduction of an autoradiogram of electrophoresed total RNA from a panel of breast cancer cell lines probed with CH13-2a12-1.

FIG. 5 shows the Northern blot analysis for RNA overabundance of the CH13-2a12-1 gene. Lanes 1–3 show the level of expression in cultured normal epithelial cells. Lanes 4–19 show the level of expression in human breast cancer cell lines. Panel A shows the pattern obtained using the CH13-2a12-1 probe; panel B shows the pattern obtained with beta-actin cDNA, a loading control.

The results are summarized in Table 5. The scoring method is the same as for Example 4. The gene corresponding to CH13-2A12-1 was duplicated in 7 out of 16 (44%) of the cells tested. Three of the positive cell lines (600PE, BT474, and MDA435) had been studied previously by comparative genomic hybridization, but had not shown amplified chromatin in the region where CH13-2A12-1 has been mapped in these studies.

RNA overabundance was observed in 13 out of 16 (81%) of the cell lines tested. Thus, 37% of the cells had achieved RNA overabundance by a mechanism other than gene duplication. We have also obtained cells from primary breast tumors, and analyzed them for duplication of the chromosome 13 gene. Ten of the 82 tumors analyzed (12%) were positive, confirming that duplication of this gene is not an artifact of in vitro culture.

The sequence of 107 bases from the 5' end of the 1.5 kb cDNA fragment is listed in FIG. 6 (SEQ ID NO:5), and showed no homology to any known gene in GenBank. One of the three possible reading frames was found to be open, with the predicted amino acid sequence of SEQ ID NO:6.

TABLE 5

Chromosome 13 Gene in Breast Cancer Cell Lines

| Source | CH13-2a12-1 Gene duplication | | CH13-2a12-1 RNA Overabundance | |
|---|---|---|---|---|
| Normal | − | 1.00* | − | 1.00** |
| 600PE | + | 2.18 | + | 5.57 |
| BT474 | + | 1.60 | + | 3.20 |
| SKBR3 | + | 1.58 | + | 4.25 |
| MDA157 | + | 2.21 | + | 3.76 |
| CAMA-1 | + | 1.41 | + | 1.99 |
| MDA231 | + | 1.65 | + | 2.09 |
| T47D | + | 1.23 | + | 1.20 |
| MDA468 | nd | | + | 6.90 |
| MDA361 | nd | | + | 2.59 |
| MDA435 | − | 0.59 | + | 3.41 |
| MDA134 | − | 0.53 | + | 2.59 |
| DU4475 | − | 0.75 | + | 1.79 |
| MDA453 | − | 0.89 | + | 1.97 |
| BT20 | − | 0.37 | − | 1.04 |
| MCF7 | − | 0.29 | − | 1.03 |
| UACC812 | − | 0.30 | − | 0.39 |
| BT468 | − | 0.47 | nd | |
| ZR-75-30 | − | 0.70 | nd | |
| Incidence (%) | 7/16 (44%) | | 13/16 (81%) | |

+ Gene duplication or RNA overabundance; − no duplication or overabundance; nd = not done
*Degree of gene duplication is reported relative to placental DNA preparations.
**Degree of RNA overabundance is reported relative to the highest level observed for several cultures of normal epithelial cells.

Example 7

Chromosome 14 Gene CH14-2a16-1

One of the cDNA obtained corresponded to a gene that mapped to Chromosome 14. Results of the analysis are summarized in Table 6. The scoring method is the same as for Example 4. The gene corresponding to CH14-2a16-1 was duplicated in 8 out of 15 (53%) of the cells tested. The sequence of 114 bases from the 5' end of the cDNA fragment is listed in FIG. 6 (SEQ ID NO:7), and showed no homology to any known gene in GenBank. One of the three possible reading frames was found to be open, with the predicted amino acid sequence of SEQ ID NO:8.

TABLE 6

Chromosome 14 Gene in Breast Cancer Cell Lines

| Source | CH14-2a16-1 Gene duplication | | CH14-2a16-1 RNA Overabundance | |
|---|---|---|---|---|
| Normal | − | 1.00* | − | 1.00** |
| BT474 | + | 2.89 | + | 2.57 |
| MCF7 | + | 1.35 | + | 1.88 |
| SKBR3 | + | 2.58 | + | 2.19 |
| T47D | + | 2.28 | nd | |
| MDA157 | + | 1.52 | + | 2.52 |
| UACC812 | + | 2.23 | nd | |
| MDA361 | − | 0.97 | + | 1.43 |
| MDA453 | + | 1.58 | + | 5.92 |
| BT20 | − | | − | 1.07 |

TABLE 6-continued

Chromosome 14 Gene in Breast Cancer Cell Lines

| Source | CH14-2a16-1 Gene duplication | | CH14-2a16-1 RNA Overabundance | |
|---|---|---|---|---|
| 600PE | − | 0.94 | + | 2.00 |
| MDA231 | + | 1.66 | + | 2.19 |
| CAMA-1 | − | 0.92 | − | 0.71 |
| DU4475 | − | 0.87 | + | 1.33 |
| BT468 | − | 0.46 | nd | |
| MDA134 | − | 0.77 | + | 7.17 |
| Incidence (%) | 8/15 (53%) | | 10/12 (83%) | |

+ Gene duplication or overabundance; − no duplication or overabundance; nd = not done
*Degree of gene duplication is reported relative to placental DNA preparations.
**Degree of RNA overabundance is reported relative to the highest level observed for several cultures of normal epithelial cells.

Example 8

Identification of Other Cancer-Associated Genes cDNA fragments corresponding to additional cancer-associated genes are obtained by applying the techniques of Examples 1 & 2 with appropriate adaptations. As before, cancer cells are selected for use in differential display of RNA, based on whether they share a duplicated chromosomal region according to Table 7:

TABLE 7

Cancer cell lines sharing duplicated chromosomal regions

| Chromosomal location | Cancer type & references |
|---|---|
| 1p22-32 | small cell (Levin 1994) |
| 1p22 | bladder (Kallioniemi 1995) |
| 1p32-33 | rabdomyosarcoma (Steilen-Gimbel); breast (Ried 1995); small cell lung (Ried 1994) |
| 1q21-22 | sarcoma (Forus 1995a & b); breast (Muleris 1994a) |
| 1q24 | small cell (Levin 1994) |
| 1q31 | bladder (Kallioniemi 1995) |
| 1q32 | glioma (Muleris 1994b; Schrock) |
| 1q | head and neck (Speicher 1995), breast (Muleris 1994a) |
| 2p23 | small cell lung (Ried 1994) |
| 2p24-25 | small cell lung (Levin 1994) |
| 2 | head and neck (Speicher 1995) |
| 2q | head and neck (Speicher 1995) |
| 2q33-36 | head and neck (Speicher 1995) |
| 3p22-24 | bladder (Voorter), small cell (Levin 1994) |
| 3q24-26 | bladder (Kallioniemi 1995), glioma (Kim), osteosarcoma (Tarkkanen) |
| 3q25-26 | ovarian (Iwabuchi) |
| 3q26-term | head and neck (Speicher 1995) |
| 3q | small cell lung (Levin 1995; Rerid 1994); head and neck (Speicher 1995) |
| 4q12 | glioma (Schrock) |
| 5p | small cell lung (Levin 1994 & 1995; Ried 1994) |
| 5p15.1 | glioma (Muleris 1994b) |
| 6p | osteosarcoma (Forus 1995a); breast (Ried 1995) |
| 6p21-term | melanoma (Speicher) |
| 7p | glioma (Schliegel 1994 & 1996; may be EGFR) |
| 7p11-12 | glioma (Muleris 1994b; Schrock), small cell lung (Ried 1994) |
| 7q21-32 | glioma (Kim; Muleris 1994b; Schrock) |
| 7q21-22 | head and neck (Speicher), glioma (Schrock) |
| 7q33-term | head and neck (Speicher 1995) |
| 7 | colon (Schlegel 1995); glioma (Kim), head and neck (Speicher); prostate (Visakorpi) |
| 8q | small cell lung (Ried 1994) |

TABLE 7-continued

Cancer cell lines sharing duplicated chromosomal regions

| Chromosomal location | Cancer type & references |
|---|---|
| 8q21 | bladder (Kallioniemi 1995) |
| 8q24 | myeloid leukemia (Mohamed) |
| 8q22–24 | glioma (Kim; Muleris 1994b); breast (Muleris 1994a) |
| 8q24–25 | small cell (Levin 1994; Ried 1994); |
| 8q23-term | sarcoma (Forus 1995a), melanoma (Speicher) |
| 8q24 | ovarian (Iwabuchi) |
| 8q | breast (Ried 1995; Isola; Muleris 1994a), small cell lung (Levin 1994 & 1995), B-cell leukemias (Bentz 1994a), myeloid leukemia (Bentz 1994b), glioma (Schlegel), head and neck (Speicher 1995), prostate (Cher, Visakorpi) |
| 9 | head and neck (Speicher) |
| 9p | head and neck (Speicher) |
| 9p2 | glioma (Muleris 1994b) |
| 9p13 | breast (Muleris 1994a) |
| 10p | head and neck (Speicher 1995) |
| 10p13–14 | bladder (Voorter) |
| 10q22 | breast (Muleris 1994a) |
| 11q13 | head and neck (Speicher 1995), breast (Muleris 1994a) |
| 12 | B-cell leukemias (Bentz 1995a) |
| 12p | head and neck (Speicher 1995), glioma (Schrock) |
| 12q | glioma (Schlegel 1994) |
| 12q12–15 | bladder (Voorter), osteosarcoma (Tarkkanen), liposarcoma (Suijkerbuijk) |
| 12q21.3–22 | liposarcoma (Suijkerbuijk) |
| 13 | colon (Schlegel 1995) |
| 13q | breast (Ried 1995), head and neck (Speicher 1995) |
| 13q21–34 | bladder (Kallioniemi 1995) |
| 13q32-term | head and neck (Speicher 1995), small cell lung (Ried 1994) |
| 14q | head and neck (Speicher 1995) |
| 15q26 | breast (Muleris 1994a) |
| 16 | head and neck (Speicher 1995) |
| 16p | breast (Ried 1995) |
| 16p11.2 | breast (Muleris 1994a) |
| 17 | head and neck (Speicher 1995) |
| 17p1.1–12 | osteosarcoma (Forus 1995a; Tarkkanen) |
| 17q | breast (Ried 1995), small cell lung (Ried 1994) |
| 17q21.1 | breast (Muleris 1994a) |
| 17q22–23 | bladder (Voorter), breast (Muleris 1994a) |
| 17q22–24 | breast (Kallioniemi 1994) |
| 18p11 | bladder (Voorter) |
| 19q13.1 | small cell lung (Ried 1994) |
| 20p | head and neck (Speicher 1995) |
| 20q | ovarian (Iwabuchi), colon (Schlegel 1995), breast (Isola; Tanner) |
| 20q13.3 | breast (Muleris 1994a), Kallioniemi (1994) |
| 22q | head and neck (Speicher 1995) |
| 22q11–13 | bladder (Voorter), glioma (Schrock) |
| X | prostate (Visakorpi) |
| Xq | small cell lung (Levin 1995) |
| Xq24 | small cell (Levin 1994) |
| Xq11–13 | prostate (Visakorpi), osteosarcoma (Tarkkanen) |

Control RNA is prepared from normal tissues to match that of the cancer cells in the experiment. Normal tissue is obtained from autopsy, biopsy, or surgical resection. Absence of neoplastic cells in the control tissue is confirmed, if necessary, by standard histological techniques. cDNA corresponding to RNA that is overabundant in cancer cells and duplicated in a proportion of the same cells is characterized further, as in Examples 3–7. Additional cDNA comprising an entire protein-product encoding region is rescued or selected according to standard molecular biology techniques: See, e.g., commonly owned U.S. patent application 06/019.202, which is incorporated herein by reference in its entirety.

REFERENCES

Articles on General Topics

1. Adnane J. et al. (1991), "BEK and FLG, two receptors to members of the FGF family, are amplified in subsets of human breast cancers", Oncogene 6:659–661.
2. Alitalo K. et al. (1986), "Oncogene amplification in tumor cells", Adv. Cancer Res. 47:235–281.
3. Altschul et al. (1986), Bull. Math. Bio. 48:603–616.
4. Beardsley T. (1994), "Crabshoot: manufacturers gamble on cancer vaccines again", Scientific American, Sept: 102.
5. Berns E. M. et al. (1992), "Sporadic amplification of the insulin-like growth factor 1 receptor gene in human breast tumors", Cancer Res. 52:1036–1039.
6. Bishop J. M. (1991), "Molecular themes in oncogenesis", Cell 64:235–248.
7. Blast R. C. Jr. (1993), "Perspectives on the future of cancer markers", Clin Chem. 31:2444–2451.
8. Brison O. (1993), "Gene amplification and tumor progression", Biochim. Biophys. Acta 1155:25–41.
9. Culver K. W. et al. (1994), "Gene therapy for cancer," Trends Genet. 10:174–178.
10. Henikoff et al. (1992), Proc. Natl. Acad. Sci. USA 89:10915–10919.
11. Kallioniemi A. et al. (1992), "Comparative genomic hybridization for molecular cytogenetic analysis of solid tumors", Science 258:818–821.
12. Kocher O. et al. (1995), "Identification of a novel gene, selectively up-regulated in human carcinomas, using the differential display technique", Clin. Cancer Res. 1:1209–1215.
13. Lippman M. E. (1993), "The development of biological therapies for breast cancer", Science 259:631–632.
14. MacLean G. D. et al. (1992), "The immune system, cancer antigens and immunotherapy", Contemp. Oncol. Aug./Sep.
15. McKenzie D. et al. (1994), "Using the RNA arbitrarily priumed polymerase chain reaction (RAP-PCR) to analyze gene expression in human breast cancer cells lines" [abstract], J. Cell. Biochem. 18D:248.
16. Muss H. B. et al. (1994), "c-erbB-2 expression and response to adjuvant therapy in women with node-positive early breast cancer", New Engl. J. Med. 330:1260–1266.
17. Morgan R. A. et al. (1993), "Human gene therapy." Annu. Rev. Biochem. 62:191–217.
18. Roth J. A. (1994), "Modulation of oncogene and tumor-suppressor gene expression: a novel strategy for cancer prevention and treatment", Ann. Surg. Oncol. 1:79–86.
19. Saint-Ruf C. et al. (1990), "Proto-oncogene amplification and homogeneously staining regions in human breast carcinomas", Genes Chromosomes Cancer 2:18–26.
20. Slamon D. J. et al. (1987), "Human breast cancer: correlation of relapse and survival with amplification of the HER-2/neu oncogene", Science 235:178–182.
21. Schwab M. et al. (1990), "Amplification of cellular oncogenes: a predictor of clinical outcome of human cancer", Genes Chromosomes Cancer 1:181–193.
22. Thompson C. T. et al. (1993), "Cytogenetic profiling using fluorescence in situ hybridization (FISH) and comparative genomic hybridization (CGH)", J. Cell. Biochem. 17G:139–143.
23. Unsigned (1994), "Synthetic vaccine stabilizes advanced cancer, prolongs survival", Oncol. News 3:1.

24. Watson M. A. et al. (1994). "Isolation of differentially expressed sequence tags from human breast cancer". Cancer Res. 54:4598–4602.

25. Watson M. A. et al. (1996). "Mammaglobulin, a mammary-specific member of the uteroglobulin gene family, is overexpressed in human breast cancer". Cancer Res. 56:860–865.

26. Zafrani B. et al. (1992). "Cytogenetic study of breast cancer". Hum Pathol 23:542–547.

Articles on Differential Display, RNA Fingerprinting, and Related Techniques

1. Ayala M. et al. (1995). "New primer strategy improves precision of differential display". BioTechniques 18:842–850.

2. Bauer D. et al. (1993). "Identification of differentially expressed mRNA species by an improved display technique (DDRT-PCR). Nucl. Acids Res. 21:4272–4280.

3. Bertioli D. J. et al. (1995). "An analysis of differential display shows a strong bias towards high copy number mRNAs". Nucl. Acids Res. 23:4520–4523.

4. Chen Z. et al. (1995). "Differential expression of human tissue factor in normal mammary epithelial cells and in carcinomas". Molecular Med. 1:153–160.

5. Haag E. et al. (1994). "Effects of primer choice and source of Taq DNA polymerase on the bainding patterns of differential display RT-PCR". BioTechniques 17:226–228.

6. Hadman M. Et al. (1995). "Modifications to the differential display technique reduce background and increase sensitivity". Anal. Biochem. 226:383–386.

7. Ito T. et al. (1994). "Fluorescent differential display: arbitrarily primed RT-PCR fingerprinting on an automated DNA sequencer". FEBS Lett. 351:231–236.

8. Liang P. et al. (1992a). "Differential display of eukaryotic messenger RNA by means of the polymerase chain reaction". Science 257:967–971.

9. Liang P. et al. (1992b). "Differential display and cloning of messenger RNAs in human breast cancer versus mammary epithelial cells". Cancer Res. 52:6966–6968.

10. Liang P. et al. (1993). "Distribution and cloning of eukaryotic mRNAs by means of differential display: refinements and optimization". Nucl. Acids Res. 21:3269–3275.

11. Liang P. et al. (1994). "Differential display using one-base anchored oligo-dT primers". Nucl. Acids Res. 22:5763–5764.

12. Liang P. et al. (1995a). "Recent advances in differential display". Curr. Opin. Immunol. 7:274–280.

13. Liang P. et al (1995b). "analysis of altered gene expression by differential display". Methods Enzymol. 254:304–321.

14. Linskens M. H. K. et al. (1995). "Cataloging altered gene expression in young and senescent cells using enhanced differential display". Nucl. Acids Res. 23:3244–3251.

15. Snager R. et al. (1993). "Identification by differential display of alpha-6 integrin as a candidate tumor suppressor gene". FASEB J. 7:964–970.

16. Sompayrac L. et al. (1995). "Overcoming limitations of the mRNA differential display technique". Nucl. Acids Res. 23:4738–4739.

17. Sun Y. et al. (1994). "Moelcular cloning of five messenger RNAs differentially expressed in preneoplastic or neoplastic JB6 mouse epidermal cells: one is homologous to human tissue inhibitor of metalloproteinases-3". Cancer Res. 54:1139–1144.

18. Sunday M. E. et al. (1995). "Differential display RT-PCR for identifying novel gene expression in the lung". Am. J. Physiol. 269:L273–L284.

19. Trentmann S. M. et al. (1995). "Alternatives to $^{35}$S as a label for the differential display of eukaryotic messenger RNA". Science 267:1186–1187.

20. Welsh J. et. al. (1992). "Arbitrarily primed PCR fingerprinting of RNA". Nucl. Acids Res. 20:4965–4970.

21. Yeatman T. J. et al. (1995). "Identification of a differentially-expressed message associated with colon cancer liver metastasis using an improved method of differential display". Nucl. Acids Res. 23:4007–4008.

22. Yoshikawa T. et al. (1995). "Detection, simultaneous display and direct sequencing of multiple nuclear hormone receptor genes using bilaterally targeted RNA fingerprinting". Biochim. Biophys. Acta 1264:63–71.

Articles on Duplicated Chromosome Regions in Cancer

1. Bentz M. et al. (1994). "Fluorescent in situ hybridization in leukemias: 'the FISH are spawning!'". Leukemia 8:1447–1452.

2. Bentz M. et al. (1995a). "Comparative genomic hybridization in chronic B-cell leukemias shows a high incidence of chomosomal gains and losses". Blood 85:3610–3618.

3. Bentz M. et al. (1995b). "Comparative genomic hybridization in the investigation of myeloid leukemias". Genes Chrom. Cancer 12:193–200.

4. Bryndorf T. et al. (1995). "Comparative genomic hybridization in clinical cytogenetics". Am. J. Hu. Genetics 57:1211–1220.

5. Cher M L. et al. (1994). "Comparative genomic hybridization, allelic imbalance, and fluorescence in situ hybridization on chromosome 8 in prostate cancer". Genes Chrom. Cancer 11:153–162.

6. Dutrillaux B. et al. (1990). "Characterization of chromosomal anomalies in human breast cancer". Cancer Genet Cytogenet 49:203–217.

7. Feuerstein B G. et al. (1995). "Molecular cytogenetic quantitation of gains and losses of genetic material from human gliomas". J. Neuro-Oncol. 24:47–55.

8. Forus A. et al. (1995a). "Comparative genomic hybridization analysis of human sarcomas: I. Occurrence of genomic imbalances and identification of a novel major amplicon at 1q21-q22 in soft tissue sarcomas". Genes Chrom. Cancer 14:8–14.

9. Forus A. et al. (1995b). "Comparative genomic hydridization analysis of human sarcomas: II. Identification of novel amplicons at 6p and 17p in osteosarcomas". Genes Chrom. Cancer 14:15–21.

10. Gordon K B. et al. (1994). "Comparative genomic hybridization in the detection of DNA copy number abnormalities in uveal melanoma". Cancer Res. 54:4764–4768.

11. Gray J W. et al. (1994). "Fluorescence in situ hybridization in cancer and radiation biology". Radiation Res. 137:275–289.

12. Houldsworth J. et al. (1994), "Comparative genomic hybridization: an overview". Am. J. Path. 145:1253–1260.

13. Isola J J. et al. (1995). "Genetic aberrations detected by comparative genomic hybridization predict outcome in node-negative breast cancer". Am. J. Path. 147:905–911.

14. Iwabuchi H. et al. (1995). "Genetic analysis of benign, low-grade, and high-grade ovarian tumors". Cancer Res. 55:6172–6180.

15. Kallioniemi A. et al. (1994), "Detection and mapping of amplified DNA sequences in breast cancer by comparative genomic hybridization", Proc. Natl. Acad. Sci. USA 91:2156–2160.

16. Kallioniemi A. et al. (1995), "Identification of gains and losses of DNA sequences in primary bladder cancer by comparative genomic hybridization", Genes Chrom. Cancer 12:213–219.

17. Kim D H. et al. (1995), "Chromosomal abnormalities in glioblastoma multiforme tumors and glioma cell lines detected by comparative genomic hybridization", Int. J. Cancer 60:812–819.

18. Levin N A. et al. (1994), "Identification of frequent novel genetic alterations in small cell lung carcinoma", Cancer Res. 5086–5091.

19. Levin N A. et al. (1995), "Identification of novel regions of altered DNA copy number in small cell lung tumors", Genes Chrom. Cancer 13:175–185.

20. Lisitsyn N A. et al. (1995), "Comparative genomic analysis of tumors: detection of DNA losses and amplification", Proc. Natl. Acad. Sci. USA 92:151–155.

21. Mohamed A N. et al. (1994), "Extrachromosomal gene amplification in acute myeloid leukemia; characterization by metaphase analysis, comparative genomic hybridization, and semi-quantitative PCR", Genes Chrom. Cancer 8:185–189.

22. Mohapatra G. et al. (1995), "Detection of multiple gains and losses of genetic material in ten glioma cell lines by comparative genomic hybridization" Genes Chrom. Cancer 13:86–93.

23. Muleris M. et al. (1994a), "Detection of DNA amplification in 17 primary breast carcinomas with homogeneously staining regions by a modified comparative genomic hybridization technique", Genes Chrom. Cancer 10:160–170.

24. Muleris M. et al. (1994b), "Oncogene amplification in human fliomas: a molecular cytogenetic analysis", Oncogene 9:2717–2722.

25. Nacheva E. et al. (1995), "Comparative genomic hybridization in acute myeloid leukemia. A comparison with G-banding and chromosome painting", Cancer Genetics Cytogenetics 82:9–16.

26. Ried T. et al. (1994), "Mapping of multiple DNA gains and losses in primary small cell lung carcinomas by comparative genomic hybridization", Cancer Res. 54:1801–1806.

27. Ried T. et al. (1995), "Comparative genomic hybridization of formalin-fixed, paraffin-embedded breast tumors reveals different patterns of chromosomal gains and losses in fibroadenomas and diploid and aneuploid carcinomas", Cancer Res. 55:5415–5423.

28. Schlegel J. et al. (1994), "Detection of amplified DNA sequences by comparative genomic in situ hybridization with human glioma tumor DNA as probe", Verhand. Deut. G. Path. 78:204–207.

29. Schlegel J. et al. (1995), "Comparative genomic in situ hybridization of colon carcinomas with replication error", Cancer Res. 55:6002–6005.

30. Schlegel J. et al. (1996), "Detection of complex genetic alterations in human glioblastoma multiforme using comparative genomic hybridization", J. Neurop à Mol. Exp. Neurol. 55:81–87.

31. Schrock E. et al. (1994), "Comparative genomic hybridization of human malignant gliomas reveals multiple amplification sites and nonrandom chromosomal gains and losses", Am. J. Path. 144:1203–1218.

32. Seruca R. et al. (1995), "Increasing levels of MYC and MET co-amplification during tumor progression of a case of gastric cancer", Cancer Genetics Cytogenetics 82:140–145.

33. Speicher M R. et al. (1994), "Chromosomal gains and losses in uveal melanomas detected by comparative genomic hybridization", Cancer Res. 54:3817–3823.

34. Speicher M R. et al. (1995), "Comparative genomic hybridization detects novel deletions and amplifications in head and neck squamous cell carcinomas", Cancer Res. 55:1010–1013.

35. Steilen-Gimbel H. et al. (1996), "A novel site of DNA amplification on chromosome 1p32–33 in a rhabdomyosarcoma revealed by comparative genomic hybridization", Hu. Genetics 97:87–90.

36. Suijkerbuijk R F. et al. (1994), "Comparative genomic hybridization as a tool to define two distinct chromosome 12-derived amplification units in well-differentiated liposarcomas", Genes Chrom Cancer 9:292–295.

37. Tanner M M. et al. (1994), "Increased copy number at 20q13 in breast cancer: defining the critical region and exclusion of candidate genes", Cancer Res. 54:4257–4260.

38. Tarkkanen M. et al. (1995), "Gains and losses of DNA sequences in osteosarcomas by comparative genomic hybridization", Cancer Res. 55:1334–1338.

39. Visakorpi T. et al. (1995a), "Genetic changes in primary and recurrent prostate cancer by comparative genomic hybridization", Cancer Res. 55:342–347.

40. Visakorpi T. et al. (1995b), "In vivo amplification of the androgen receptor gene and progression of human prostate cancer", Nature Genetics 9:401–406.

41. Voorter C. et al. (1995), "Detection of chromosomal imbalances in transitional cell carcinoma of the bladder by comparative genomic hybridization", Am. J. Path. 146:1341–1354.

42. Wiltshire R N. et al. (1995), "Direct visualization of the clonal progression of primary cutaneous melanoma: application of tissue microdissection and comparative genomic hybridization", Cancer Res. 55:3954–3957.

| U.S. Patents | | | |
|---|---|---|---|
| US 4,444,887 | 4/1984 | Hoffman M. K. | (mAB method) |
| US 4,472,500 | 9/1984 | Milstein C. et al | (mAB cell) |
| US 4,491,632 | 1/1985 | Wands J. R. et al. | (HBV mAb) |
| US 4,683,195 | 7/1987 | Mullis K. B. | (PCR) |
| US 4,683,202 | 7/1987 | Mullis K. B. et al. | (PCR) |
| US 4,968,603 | 11/1990 | Slamon D. J. et al. | (erbB2 in diagnosis) |
| US 5,124,246 | 6/1992 | Urdea M. S. et al. | (branched DNA) |
| US 5,262,311 | 16/1993 | Pardee A. B. et al. | (differential display) |
| US 5,399,346 | 11/1995 | Anderson W. F. et al. | (gene therapy) |
| US 5,427,932 | 6/1995 | Weier H. -U. G. et al. | (repeat sequence probes) |
| US 5,447,841 | 9/1995 | Gray J. W. et al. | (chromosome staining) |
| US 5,472,842 | 9/1995 | Stokke T. et al. | (detecting amplicons) |
| Other Patent Publications | | | |
| EP 430402 | 1991 | Gray J. W. et al. | (chromosome staining) |
| EP 500290 | 1992 | Gray J. W. et al. | (chromosome staining) |

| | | | |
|---|---|---|---|
| WO 93/08701 | 1993 | Goldstein, J. A. et al. | (c-myc) |
| WO 93/18176 | 1993 | Liang P. et al. | (mRNA cloning method) |
| WO 93/18186 | 1993 | Gray J. W. et al. | (CGH method) |
| WO 94/00136 | 1994 | Kasprzyk P. G. et al. | (anti-erb in therapy) |
| WO 94/00601 | 1994 | Levine A. J. et al. | (mAB in diagnosis) |
| WO 94/17414 | 1994 | Keyomarsi K. et al. | (detection) |
| WO 94/28127 | 1994 | Sikora K. et al. | (erb promoter) |
| WO 95/09929 | 1995 | Gray J. W. et al. | (abnormal chromosomes) |
| WO 95/22624 | 1995 | Christman M. F. et al. | (changes in lung cancer) |
| WO 95/33760 | 1995 | Gullans S. et al. | (nested primers) |

We claim:

1. A method for obtaining cDNA from a gene that is duplicated or overexpressed in cancer, comprising the steps of:

a) supplying an RNA preparation from control cells;

b) supplying RNA preparations from at least two cancer cells from different individuals, wherein the two cancer cells share a duplicated gene;

c) displaying cDNA reverse transcribed from the RNA preparations of step a) and step b) such that cDNA from different RNA in each preparation are displayed separately;

d) isolating cDNA from step c) that is preferentially displayed in the cancer cells relative to the control cells;

e) supplying a digested DNA preparation from control cells;

f) supplying digested DNA preparations from at least two cancer cells from different individuals;

g) hybridizing the cDNA isolated in step d) with each of the digested DNA preparations of step e) and step f); and h) identifying cDNA that hybridizes preferentially in step g) with the DNA from the cancer cells relative to the DNA of the control cells.

2. The method of claim 1, wherein RNA preparations from at least three cancer cells from different individuals that share a duplicated gene are supplied in step b).

3. The method of claim 1, wherein the control cells of step a) are not grown in vitro.

4. The method of claim 1, wherein the cancer cells used for supplying the RNA preparations in step b) share a duplicated chromosomal band.

5. The method of claim 1, wherein the cancer cells used for supplying the digested DNA preparations in step f) share a duplicated chromosomal band.

6. The method of claim 1, wherein the two different cancer cells from different individuals used for supplying the RNA preparations in step b) are both obtained from cancer cell lines grown ex vivo.

7. The method of claim 1, further comprising supplying a digested mitochondrial DNA preparation; hybridizing the cDNA identified in step h) with the digested mitochondrial DNA preparation; and identifying cDNA from the cDNA of step h) that does not hybridize with the digested mitochondrial DNA preparation.

8. The method of claim 1, further comprising the steps of:

i) supplying an RNA preparation from control cells;

j) supplying RNA preparations from at least two cancer cells from different individuals;

k) hybridizing the cDNA of step h) with each of the RNA preparations of step i) and step j); and l) identifying cDNA from the cDNA of step h) that hybridizes preferentially in step k) with RNA from the cancer cells relative to the RNA from the control cells.

9. The method of claim 8, wherein the gene to which the cDNA corresponds is not duplicated in at least one of the cancer cells used to supply the RNA in step j).

10. The method of claim 1, wherein the two different cancer cells used to supply the RNA preparations in step b) are breast cancer cells.

11. The method of claim 1, wherein the two different cancer cells used to supply the RNA preparations in step b) are from a common type of cancer, wherein the type of cancer is selected from the group consisting of lung cancer, glioblastoma, pancreatic cancer, colon cancer, prostate cancer, hepatoma, and myeloma.

12. The method of claim 1, wherein the two different cancer cells used to supply the digested DNA preparations in step f) are breast cancer cells.

13. The method of claim 1, wherein the two different cancer cells used to supply the digested DNA preparations in step f) are from a common type of cancer, wherein the type of cancer is selected from the group consisting of lung cancer, glioblastoma, pancreatic cancer, colon cancer, prostate cancer, hepatoma, and myeloma.

14. A method for characterizing a gene that is duplicated or overexpressed in cancer, comprising obtaining cDNA from the gene according to the method of claim 1, and then sequencing the cDNA.

15. A method for obtaining cDNA from a gene that is duplicated or overexpressed in cancer, comprising the steps of:

a) supplying an RNA preparation from control cells;

b) supplying RNA preparations from at least two different cancer cells from different individuals, wherein the two cancer cells share a duplicated gene;

c) displaying cDNA reverse transcribed from the RNA preparations of step a) and step b) such that cDNA from different RNA in each preparation are displayed separately; and d) isolating cDNA from step c) that is preferentially displayed in the cancer cells relative to the control cells.

16. The method of claim 15, wherein the two different cancer cells used to supply the RNA preparations in step b) are breast cancer cells.

17. The method of claim 15, wherein the cancer cells used for supplying the RNA preparations in step b) share a duplicated chromosomal band.

18. The method of claim 15, wherein RNA preparations from at least three cancer cells from different individuals are supplied in step b), and the three cancer cells from different individuals share a duplicated chromosomal band.

19. The method of claim 1, wherein the two different cancer cells used to supply the RNA preparations in step b) are from a common type of cancer, wherein the type of cancer is selected from the group consisting of lung cancer, glioblastoma, pancreatic cancer, colon cancer, prostate cancer, hepatoma, and myeloma.

20. A method for obtaining cDNA from a gene that is deleted or underexpressed in cancer, comprising the steps of:

a) supplying an RNA preparation from control cells;

b) supplying RNA preparations from at least two different cancer cells from different individuals, wherein the two cancer cells share a deleted gene;

c) displaying cDNA reverse transcribed from the RNA preparations of step a) and step b) such that cDNA from different RNA in each preparation are displayed separately; and d) isolating cDNA from step c) that is preferentially displayed in the control cells relative to the cancer cells.

21. The method of claim 20, further comprising the steps of:

e) supplying a digested DNA preparation from control cells;

f) supplying digested DNA preparations from at least two cancer cells from different individuals;

g) hybridizing the cDNA isolated in step d) with each of the digested DNA preparations of step e) and step f); and h) identifying cDNA that hybridizes preferentially in step g) with the DNA from the control cells relative to the DNA of the cancer cells.

22. A method for characterizing a gene that is duplicated or overexpressed in cancer, comprising obtaining cDNA corresponding to the gene according to the method of claim 15, and then sequencing the cDNA.

* * * * *